(12) United States Patent
Ladika et al.

(10) Patent No.: US 6,709,742 B2
(45) Date of Patent: Mar. 23, 2004

(54) CROSSLINKED ELASTIC FIBERS

(75) Inventors: Mladen Ladika, Midland, MI (US); John Klier, Midland, MI (US); Ashish Sen, Midland, MI (US); Erin D. O'Driscoll, Midland, MI (US); Nancy J. Schrock, Lake Jackson, TX (US); Antonio Batistini, Adliswil (CH)

(73) Assignee: Dow Global Technologies Inc., Midland, MI (US)

( * ) Notice: Subject to any disclaimer, the term of this patent is extended or adjusted under 35 U.S.C. 154(b) by 52 days.

(21) Appl. No.: 09/945,532

(22) Filed: Aug. 31, 2001

(65) Prior Publication Data

US 2002/0064653 A1 May 30, 2002

Related U.S. Application Data

(63) Continuation-in-part of application No. 09/313,740, filed on May 18, 1999, now Pat. No. 6,500,540.
(60) Provisional application No. 60/086,059, filed on May 18, 1998.

(51) Int. Cl.[7] .............................. D02G 3/00; C08K 3/28
(52) U.S. Cl. ...................... 428/364; 428/394; 428/395; 522/75
(58) Field of Search ................... 428/364, 394, 428/395; 522/75

(56) References Cited

U.S. PATENT DOCUMENTS

| | | | |
|---|---|---|---|
| 2,957,512 A | 10/1960 | Wade et al. | 154/33.05 |
| 3,058,944 A | 10/1962 | Breslow et al. | 260/41 |
| 3,156,242 A | 11/1964 | Crowe, Jr. | 128/296 |

(List continued on next page.)

FOREIGN PATENT DOCUMENTS

| | | | |
|---|---|---|---|
| CA | 935598 | * | 10/1973 |
| DE | 2337813 | | 2/1974 |
| EP | 0 416 815 A2 | | 3/1991 |

(List continued on next page.)

OTHER PUBLICATIONS

Cady, L.D., *The Role of Comonomer Type and Distribution in LLDPE Product Performance,* SPE Regional Technical Conference, Quaker Square Hilton, Akron, Ohio, 1985, pp. 107–119.

Dealy, J., *Rheometers for Molten Plastics,* Van Nostrand Reinhold Co., (1982), pp. 97–99.

(List continued on next page.)

*Primary Examiner*—Cynthia H. Kelly
*Assistant Examiner*—J. M. Gray
(74) *Attorney, Agent, or Firm*—Whyte Hirschboeck Dudek SC

(57) ABSTRACT

Elastic fibers are described that comprise (i) a polyolefin polymer, e.g., a homogeneously branched, preferably substantially linear, ethylene polymer, and (ii) a photoinitiator, e.g., an aromatic ketone, in an amount sufficient to effect at least a partial cross-linking of the polymer when the fiber is exposed to sufficient UV-radiation to activate the photoinitiator. Articles, e.g., fabrics, comprising fibers of this invention, either alone or in combination with one or more other fibers, e.g., cellulose, nylon, etc., exhibit good heat resistance and elasticity at elevated temperatures.

57 Claims, 6 Drawing Sheets

Dynamic Mechanical Analysis of Polymer A Film Crosslinked with 1 wt% Irgacure 651

U.S. PATENT DOCUMENTS

| | | | |
|---|---|---|---|
| 3,485,706 A | 12/1969 | Evans | 161/72 |
| 3,520,861 A | 7/1970 | Thomson et al. | 260/88.1 |
| 3,645,992 A | 2/1972 | Elston | 260/80.78 |
| 3,881,489 A | 5/1975 | Hartwell | 128/287 |
| 3,989,867 A | 11/1976 | Sisson | 428/132 |
| 4,076,698 A | 2/1978 | Anderson et al. | 526/348.6 |
| 4,190,602 A | 2/1980 | Brunisholz et al. | 260/590 |
| 4,322,027 A | 3/1982 | Reba | 226/97 |
| 4,340,563 A | 7/1982 | Appel et al. | 264/518 |
| 4,381,781 A | 5/1983 | Sciaraffa et al. | 604/372 |
| 4,413,110 A | 11/1983 | Kavesh et al. | 526/348.1 |
| 4,500,648 A | 2/1985 | Malpass | 502/115 |
| 4,599,392 A | 7/1986 | McKinney et al. | 526/318.6 |
| 4,190,602 A | 5/1987 | Brunisholz et al. | 568/315 |
| 4,663,220 A | 5/1987 | Wisneski et al. | 428/221 |
| 4,668,566 A | 5/1987 | Braun | 428/286 |
| 4,798,081 A | 1/1989 | Hazlitt et al. | 73/53 |
| 4,801,482 A | 1/1989 | Goggans et al. | 428/68 |
| 4,879,170 A | 11/1989 | Radwanski et al. | 428/233 |
| 4,939,016 A | 7/1990 | Radwanski et al. | 428/152 |
| 4,940,464 A | 7/1990 | VanGompel et al. | 604/396 |
| 4,981,747 A | 1/1991 | Morman | 428/198 |
| 4,988,781 A | 1/1991 | McKinney et al. | 526/68 |
| 5,008,204 A | 4/1991 | Stehling | 436/85 |
| 5,026,798 A | 6/1991 | Canich | 526/127 |
| 5,037,416 A | 8/1991 | Allen et al. | 604/385.1 |
| 5,055,438 A | 10/1991 | Canich | 502/117 |
| 5,064,802 A | 11/1991 | Stevens et al. | 502/155 |
| 5,085,654 A | 2/1992 | Buell | 604/370 |
| 5,089,321 A | 2/1992 | Chum et al. | 428/218 |
| 5,108,820 A | 4/1992 | Kaneko et al. | 428/198 |
| 5,272,236 A | 12/1993 | Lai et al. | 526/348.5 |
| 5,278,272 A | 1/1994 | Lai et al. | 526/348.5 |
| 5,292,845 A | 3/1994 | Kawasaki et al. | 526/336 |
| 5,322,728 A | 6/1994 | Davey et al. | 428/296 |
| 5,324,576 A | 6/1994 | Reed et al. | 428/224 |
| 5,336,552 A | 8/1994 | Strack et al. | 428/224 |
| 5,380,810 A | 1/1995 | Lai et al. | 526/352 |
| 5,382,400 A | 1/1995 | Pike et al. | 264/168 |
| 5,384,373 A | 1/1995 | McKinney et al. | 526/212 |
| 5,472,775 A | 12/1995 | Obijeski et al. | 428/220 |
| 5,525,257 A | 6/1996 | Kleinstuck et al. | 252/181 |
| 5,645,542 A | 7/1997 | Anjur et al. | 604/368 |
| 5,665,800 A | 9/1997 | Lai et al. | 524/115 |
| 5,824,718 A | 10/1998 | Penfold et al. | 522/120 |
| 5,883,188 A | 3/1999 | Hwang et al. | 525/71 |
| 6,140,442 A | 10/2000 | Knight et al. | 526/348.1 |
| 6,172,165 B1 | 1/2001 | Hucul et al. | 525/326.8 |
| 6,207,237 B1 | 3/2001 | Haffner | 427/394 |
| 6,211,302 B1 | 4/2001 | Ho et al. | 525/333.5 |
| 6,225,243 B1 | 5/2001 | Austin | 442/361 |
| 6,284,842 B1 | 9/2001 | Ho et al. | 525/194 |

FOREIGN PATENT DOCUMENTS

| | | |
|---|---|---|
| EP | 0 490 854 B1 | 6/1992 |
| EP | 0 515 203 A2 | 11/1992 |
| EP | 0 748 846 A2 | 12/1996 |
| WO | 90/01521 | 2/1990 |
| WO | 94/25515 | 11/1994 |
| WO | 95/29197 | 11/1995 |
| WO | 97/26297 | 7/1997 |
| WO | 98/26001 | 6/1998 |
| WO | 99/10395 | 3/1999 |
| WO | 99/60060 | 11/1999 |
| WO | 99/63021 | 12/1999 |

OTHER PUBLICATIONS

Kirk–Othmer, *The Encyclopedia of Chemical Technology*, Third Edition, John Wiley & Sons, New York, 1981, vol. 16, pp. 416–417.

Kirk–Othmer, *The Encyclopedia of Chemical Technology*, Third Edition, John Wiley & Sons, New York, 1981, vol. 18, pp. 191–192.

Ramamurthy, A.V., *Wall Slip in Viscous Fluids and Influence of Materials of Construction*, John Wiley & Sons, Inc., Journal of Rheology, 30(2), 337–357 (1986).

Randall, J., *A Review of High Resolution Liquid $^{13}$ Carbon Nuclear Magnetic Resonance Characterizations of Ethylene–Based Polymers*, Rev. Macromol. Chem. Phys., C29(2 & 3), pp. 201–317 (1989).

Shida, M., et al., *Correlation of Low Density Polyethylene Rheological Measurements with Optical and Processing Properties*, Polymer Engineering and Science, Nov., 1977, vol. 17, No. 11, pp. 769–774.

Rudin, A., *Measurement of Long–Chain Branch Frequency in Synthetic Polymers*, Modern Methods of Polymer Characterization, John Wiley & Sons, Inc., 1991, pp. 103–112.

Wild, L., et al., *Determination of Branching Distributions in Polyethylene and Ethylene Copolymers*, Journal of Polymer Science: Polymer Physics Edition, vol. 20, pp. 441–455, 1982.

Williams, T., et al., *The Construction of a Polyethylene Calibration Curve for Gel Permeation Chromatography Using Polystyrene Fractions*, Polymer Letters, vol. 6, pp. 621–624, 1968.

Zimm, B., et al. *The Dimensions of Chain Molecules Containing Branches and Rings*, The Journal of Chemical Physics, vol. 17, No. 12, pp. 1301–1314, 1949.

Banks, J.T. et al., *Thermal and Photochemical Fragmentation of α,α–Dialkoxybenzyl Radicals: A Comparison of the Thermal Reactions with Laser Induced Fragmentations by Using Laser Flash with Laser–Jet Photolyses*, J. Am. Chem. Soc., vol. 115, pp. 2473–2477, 1993.

Bigg, D.M., et al., *Effect of Copolymer Ratio on the Crystallinity and Properties of Polylactic Acid Copolymers*, ANTEC '96, vol. 11–Materials, pp. 2028–2039, May, 1996.

Eaton, Christopher J., *Foam Extrusion*, Modern Plastics Encyclopedia, pp. 256–257, 1989.

Schwartz, Seymour S., et al., Plastics Materials and Processes, pp. 527–563, 632–647 and 596–602, 1982.

Turro, Nicholas J., et al., *Molecular Photochemistry of Alkanones in Solution: α–Cleavage, Hydrogen Abstraction, Cycloaddition, and Sensitization Reactions*, Accounts of Chemical Research, vol. 5, pp. 92–101, 1972.

\* cited by examiner

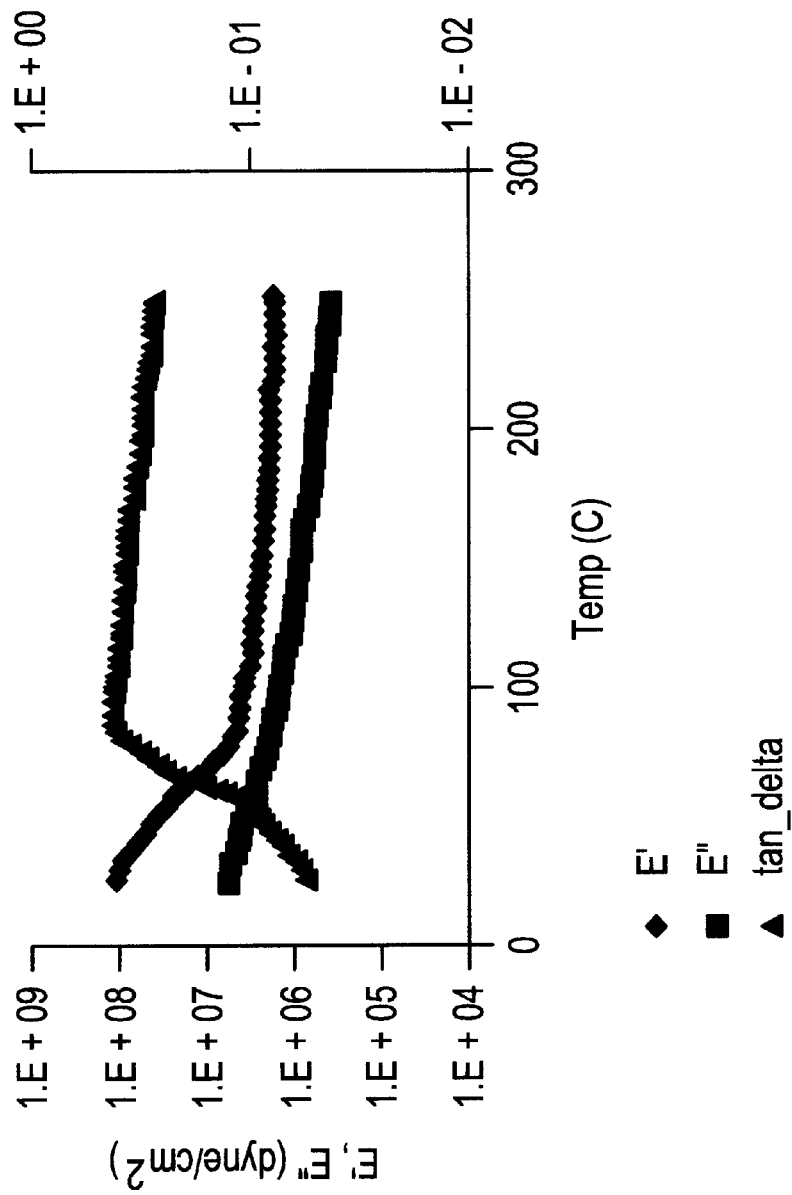

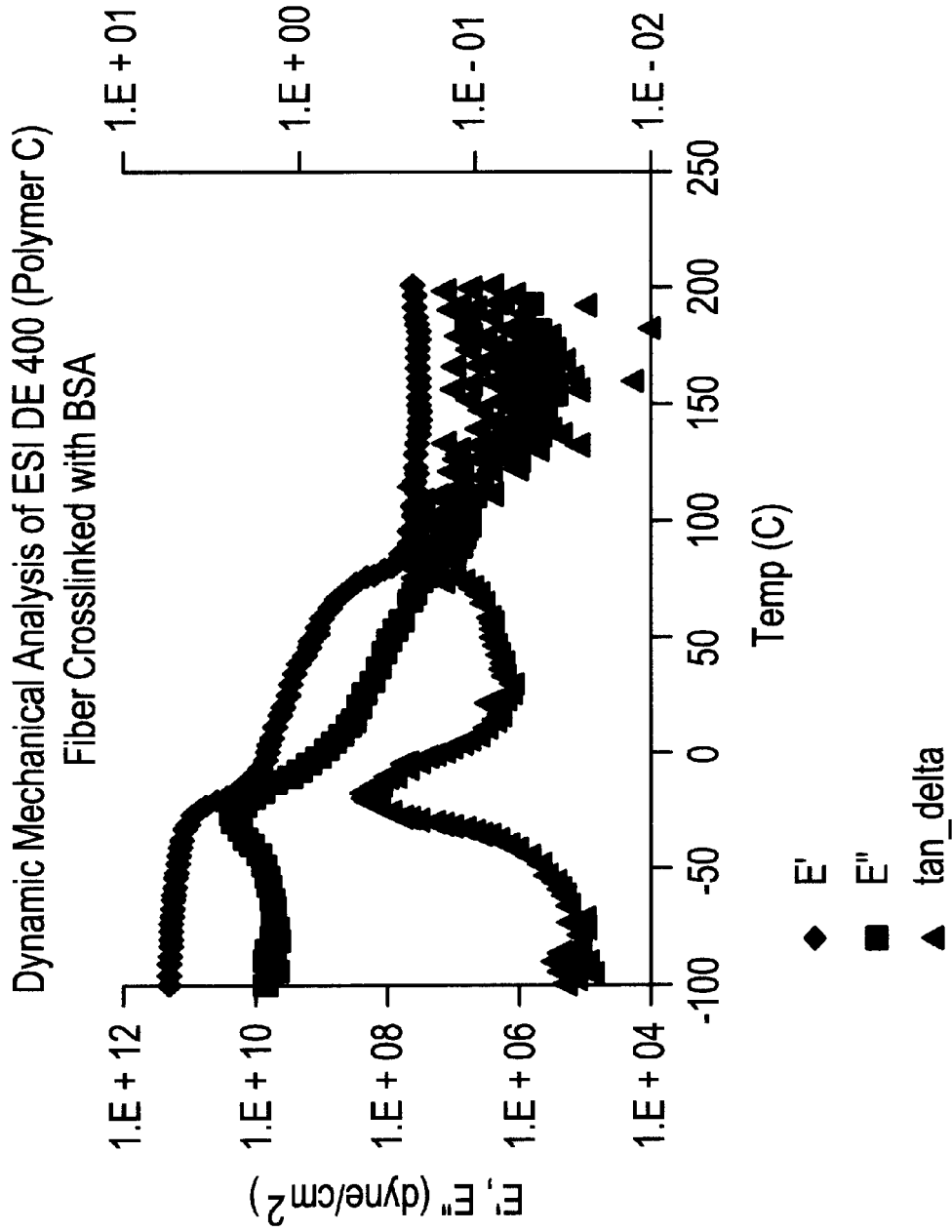

CROSSLINKED ELASTIC FIBERS

CROSS-REFERENCE TO RELATED APPLICATION

This is a continuation-in-part of application U.S. Ser. No. 09/313,740 filed May 18, 1999 now U.S. Pat. No. 6,500,540. This application claims the benefit of provisional application 60/086,059 filed on Sep. 18, 1998.

FIELD OF THE INVENTION

This invention relates to fibers. In one aspect, the invention relates to fibers comprising a polyolefin polymer and a photoinitiator while in another aspect, the invention relates to such fibers crosslinked through the action of ultraviolet (UV) radiation. Other aspects of the invention include a method of making the fiber, and structures made from the fibers.

BACKGROUND OF THE INVENTION

Fibers with excellent elasticity are needed to manufacture a variety of fabrics which are used, in turn, to manufacture a variety of durable articles such as, for example, sport apparel and furniture upholstery. Elasticity is a performance attribute, and it is one measure of the ability of a fabric to conform to the body of a wearer or to the frame of an item. Preferably, the fabric will maintain its conforming fit during repeated use, extensions and retractions at body and other elevated temperatures (such as those experienced during the washing and drying of the fabric).

Fibers are typically characterized as elastic if they have a high percent elastic recovery (that is, a low percent permanent set) after application of a biasing force. Ideally, elastic materials are characterized by a combination of three important properties: (i) a low percent permanent set, (ii) a low stress or load at strain, and (iii) a low percent stress or load relaxation. In other words, elastic materials are characterized as having the following properties (i) a low stress or load requirement to stretch the material, (ii) no or low relaxing of the stress or unloading once the material is stretched, and (iii) complete or high recovery to original dimensions after the stretching, biasing or straining is discontinued.

Spandex is a segmented polyurethane elastic material known to exhibit nearly ideal elastic properties. However, spandex is cost prohibitive for many applications. Also, spandex exhibits poor environmental resistance to ozone, chlorine and high temperature, especially in the presence of moisture. Such properties, particularly the lack of resistance to chlorine, causes spandex to pose distinct disadvantages in apparel applications, such as swimwear and in white garments that are desirably laundered in the presence of chlorine bleach.

Elastic materials comprising polyolefins, including homogeneously branched linear or substantially linear ethylene/α-olefin interpolymers, are known, e.g., U.S. Pat. Nos. 5,272,236, 5,278,272, 5,322,728, 5,380,810, 5,472,775, 5,645,542, 6,140,442 and 6,225,243. These materials are also know to exhibit good resistance to ozone, chlorine and high temperature, especially in the presence of moisture. However, polyolefin polymer materials are also know to shrink upon exposure to elevated temperatures, i.e., temperatures in excess of ambient or room temperature.

The concept of crosslinking polyethylene with UV-light in the presence of a photoinitiator was first published in the 1956. After this, the photocrosslinking of polyolefins became the subject of a substantial amount of research. The majority of this work focused on the crosslinking of polyethylene using as the photoinitiator an aromatic ketone in which the carbonyl group is linked to two aromatic groups. Upon UV-irradiation, the carbonyl group is excited into a triplet state in which it can abstract a hydrogen atom from a suitable donor.

EP 0 490 854 B1 describes a process and equipment for the continuous crosslinking of polymeric materials, in particular polyethylene, using UV-light and both a photoinitiator and a crosslinker. The photoinitiator is a benzophenone derivative with high molecular weight and low vapor pressure and a representative crosslinker is triallyl cyanurate.

U.S. Pat. No. 4,190,602 and Ger. Offen. 2,337,813 describe UV-curing of polyester resins using monoacetals of aromatic 1,2 diketones. In one example, photocrosslinking of polyethylene with Irgacure 651 (a monoacetal of aromatic 1,2 diketone) is described. In that procedure, the Irgacure 651 was worked into polyethylene of density 0.92 using mixing rolls, and the resulting rolled sheet was compression molded into 0.1 mm thick film. This film was irradiated for 40 minutes with a high-pressure mercury lamp and extracted in boiling toluene for 5 hours to give 24% of insoluble material. This example was limited to film structures.

As suggested above, much of the reported literature on the photocrosslinking of a polyolefin is limited to the photocrosslinking of a polyethylene or polypropylene resin. In many reported examples, both a photoinitiator and a photocrosslinker are required for efficient photocrosslinking. This is particularly the case with benzophenone and its derivatives, which often required a multifunctional photocrosslinker.

SUMMARY OF THE INVENTION

According to one embodiment of this invention, a temperature-stable, elastic, polyolefin polymer filament fiber substantially crosslinked solely as a result of a photoinitiator activated by exposure to UV-radiation, i.e., without the use of a photocrosslinker, is described. In another embodiment, the photoinitiator is an aromatic ketone, e.g., benzophenone, anthrone or one of their derivatives. In another embodiment, the polyolefin polymer fiber contains both a photoinitiator and a photocrosslinker, preferably a multifunctional photocrosslinker, e.g., a triallylisocyanurate.

In another embodiment of the invention a temperature-stable, substantially crosslinked, elastic fiber is prepared by a process comprising the steps of (a) providing a mixture of a polyolefin polymer and a photoinitiator; (b) forming the mixture into a fiber; and (c) exposing the fiber to UV-light for a duration sufficient to cause the fiber to have a gel level of at least 30 weight percent, as determined by ASTM D-2765. In a variation on this embodiment, the mixture includes a photocrosslinker. In another variation on this embodiment, the fiber is first formed from the polyolefin polymer, and then the photoinitiator and/or photocrosslinker is applied to the fiber.

In another embodiment of this invention, the temperature-stable, substantially crosslinked, polyolefin polymer elastic fiber is used to make a yarn, either covered or uncovered. Other embodiments of the invention include woven, nonwoven and knitted fabrics comprising one or more of the elastic fibers or yarn of the invention, and elastic structures or articles comprising one or more of the fibers of the invention.

BRIEF DESCRIPTION OF THE DRAWINGS

FIG. 1 is a graph showing the storage modulus E' of the film prepared in Example 1

FIG. 6 is a graph showing the storage modules E' of the fiber prepared in Example 11.

DETAILED DESCRIPTION OF THE INVENTION

General Definitions

Figure 2A:
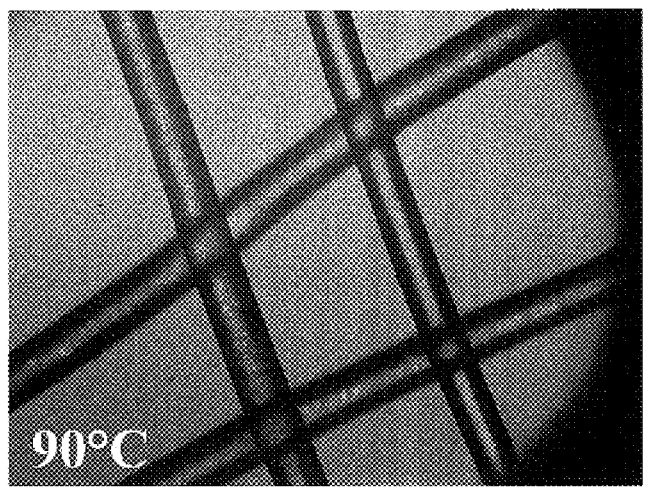
FIGS. 2A–2C are micrographs of the fiber produced in Example 4.

"Fiber" means a material in which the length to diameter ratio is greater than about 10. Fiber is typically classified according to its diameter. Filament fiber is generally defined as having an individual fiber diameter greater than about 15 denier, usually greater than about 30 denier per filament. Fine denier fiber generally refers to a fiber having a diameter less than about 15 denier per filament. Microdenier fiber is generally defined as fiber having a diameter less than about 100 microns denier per filament.

"Filament fiber" or "monofilament fiber" means a continuous strand of material of indefinite (i.e., not predetermined) length, as opposed to a "staple fiber" which is a discontinuous strand of material of definite length (i.e., a strand which has been cut or otherwise divided into segments of a predetermined length).

"Photoinitiator" means a chemical composition that, upon exposure to UV-radiation, generates radical sites on a polyolefin polymer chain without covalently bonding to the chain.

"Photocrosslinker" means a chemical composition that, in the presence of a radical-generating initiator, forms a covalent crosslink between two polyolefin polymer chains.

"Photoinitiator/crosslinker" means a chemical composition that upon exposure to UV-radiation generates two or more reactive species (e.g., free radicals, carbenes, nitrenes, etc.) that can form a covalent crosslink between two polyolefin polymer chains.

"Polyolefin polymer" means a thermoplastic polymer derived from one or more simple olefins. The polyolefin polymer can bear one or more substituents, e.g., a functional group such as a carbonyl, sulfide, etc. For purposes of this invention, "olefins" include aliphatic, alicyclic and aromatic compounds having one or more double bonds. Representative olefins include ethylene, propylene, 1-butene, 1-hexene, 1-octene, 4-methyl-1-pentene, butadiene, cyclohexene, dicyclopentadiene, styrene, toluene, α-methylstyrene and the like.

"UV-radiation", "UV-light" and similar terms mean the range of radiation over the electromagnetic spectrum from about 150 to about 700 nanometers in wavelength. For purposes of this invention, UV-radiation includes visible light.

"Temperature-stable" and similar terms mean that the fiber or other structure or article comprising the polyolefin polymer of this invention will substantially maintain its elasticity during repeated extensions and retractions after exposure to about 200 F., e.g., temperatures such as those experienced during the manufacture, processing (e.g., dying) and/or cleaning of a fabric made from the structure or article.

"Elastic" means that a fiber will recover at least about 50 percent of its stretched length after the first pull and after the fourth to 100% strain (doubled the length). Elasticity can also be described by the "permanent set" of the fiber. Permanent set is the converse of elasticity. A fiber is stretched to a certain point and subsequently released to the original position before stretch, and then stretched again. The point at which the fiber begins to pull a load is designated as the percent permanent set. "Elastic materials" are also referred to in the art as "elastomers" and "elastomeric". Elastic material (sometimes referred to as an elastic article) includes the polyolefin polymer itself as well as, but not limited to, the polyolefin polymer in the form of a fiber, film, strip, tape, ribbon, sheet, coating, molding and the like. The preferred elastic material is fiber. The elastic material can be either cured or uncured, radiated or unradiated, and/or crosslinked or uncrosslinked.

"Nonelastic material" means a material, e.g., a fiber, that is not elastic as defined above.

"Radiated" or "irradiated" means that the polyolefin polymer, shaped or in the form of an article, was subjected to the source of UV-radiation operated at the power of at least about 50 watts whether or not there was a measurable decrease in percent xylene extractables (i.e., an increase in insoluble gel).

"Substantially crosslinked" and similar terms mean that the polyolefin polymer, shaped or in the form of an article, has xylene extractables of less than or equal to 70 weight percent (i.e., greater than or equal to 30 weight percent gel content), preferably less than or equal to 40 weight percent (i.e., greater than or equal to 60 weight percent gel content). Xylene extractables (and gel content) are determined in accordance with ASTM D-2765.

"Cured" and "substantially cured" mean that the polyolefin polymer, shaped or in the form of an article, was subjected or exposed to a treatment which induced substantial crosslinking.

"Curable" and "crosslinkable" mean that the polyolefin polymer, shaped or in the form of an article, is not cured or crosslinked and has not been subjected or exposed to treatment that has induced substantial crosslinking (although the polyolefin polymer, shaped or in the form of an article, comprises additive(s) or functionality which will effectuate substantial crosslinking upon subjection or exposure to such treatment).

In the practice of this invention, curing, irradiation or crosslinking is accomplished by UV-radiation. Suitable UV-radiation equipment is available from Fusion UV Systems, Inc. and American Ultraviolet Company.

"Homofil fiber" means a fiber that has a single polymer region or domain, and that does not have any other distinct polymer regions (as do bicomponent fibers).

"Bicomponent fiber" means a fiber that has two or more distinct polymer regions or domains. Bicomponent fibers are also know as conjugated or multicomponent fibers. The polymers are usually different from each other although two or more components may comprise the same polymer. The polymers are arranged in substantially distinct zones across the cross-section of the bicomponent fiber, and usually extend continuously along the length of the bicomponent fiber. The configuration of a bicomponent fiber can be, for example, a sheath/core arrangement (in which one polymer is surrounded by another), a side by side arrangement, a pie arrangement or an "islands-in-the sea" arrangement. Bicomponent fibers are further described in U.S. Pat. Nos. 6,225,243, 6,140,442, 5,382,400, 5,336,552 and 5,108,820.

"Meltblown fibers" are fibers formed by extruding a molten thermoplastic polymer composition through a plurality of fine, usually circular, die capillaries as molten threads or filaments into converging high velocity gas streams (e.g. air) which function to attenuate the threads or filaments to reduced diameters. The filaments or threads are carried by the high velocity gas streams and deposited on a collecting surface to form a web of randomly dispersed fibers with average diameters generally smaller than 10 microns.

"Meltspun fibers" are fibers formed by melting at least one polymer and then drawing the fiber in the melt to a diameter (or other cross-section shape) less than the diameter (or other cross-section shape) of the die.

"Spunbond fibers" are fibers formed by extruding a molten thermoplastic polymer composition as filaments through a plurality of fine, usually circular, die capillaries of a spinneret. The diameter of the extruded filaments is rapidly reduced, and then the filaments are deposited onto a collecting surface to form a web of randomly dispersed fibers with average diameters generally between about 7 and about 30 microns.

"Nonwoven" means a web or fabric having a structure of individual fibers or threads which are randomly interlaid, but not in an identifiable manner as is the case of a knitted fabric. The elastic fiber of the present invention can be employed to prepare nonwoven structures as well as composite structures of elastic nonwoven fabric in combination with nonelastic materials.

"Yarn" means a continuous length of twisted or otherwise entangled filaments which can be used in the manufacture of woven or knitted fabrics and other articles. Yarn can be covered or uncovered. Covered yarn is yarn at least partially wrapped within an outer covering of another fiber or material, typically a natural fiber such as cotton or wool.

Polyolefin Polymers

While a variety of polyolefin polymers can be used in the practice of this invention (e.g., polyethylene, polypropylene, ethylene/styrene interpolymers (ESI), and catalytically modified polymers (CMP), e.g., partially or fully hydrogenated polystyrene or styrene/butadiene/styrene block copolymers, polyvinylcyclohexane, etc.), ethylene polymers are the preferred polyolefin polymers. Homogeneously branched ethylene polymers are more preferred and homogeneously branched, substantially linear ethylene interpolymers are especially preferred.

"Polymer" means a polymeric compound prepared by polymerizing monomers, whether of the same or a different type. The generic term "polymer" embraces the terms "homopolymer," "copolymer," "terpolymer" as well as "interpolymer." "Interpolymer" means a polymer prepared by the polymerization of at least two different types of monomers. The generic term "interpolymer" includes the term "copolymer" (which is usually employed to refer to a polymer prepared from two different monomers) as well as the term "terpolymer" (which is usually employed to refer to a polymer prepared from three different types of monomers).

"Catalytically modified polymer" means a hydrogenated aromatic polymer such as those taught in U.S. Pat. No. 6,172,165. Illustrative CMPs include the hydrogenated block copolymers of a vinyl aromatic compound and a conjugated diene, e.g., a hydrogenated block copolymer of styrene and a conjugated diene.

"Homogeneously branched ethylene polymer" means an ethylene/α-olefin interpolymer in which the comonomer(s) is (are) randomly distributed within a given polymer molecule, and in which substantially all of the polymer molecules have the same ethylene to comonomer molar ratio. The term refers to an ethylene interpolymer that is manufactured using so-called homogeneous or single-site catalyst systems known in the art as Ziegler vanadium, hafnium and zirconium catalyst systems, metallocene catalyst systems, or constrained geometry catalyst systems.

The ethylene polymers used in the present invention are interpolymers of ethylene with at least one $C_3$–$C_{20}$ α-olefin and/or $C_4$–$C_{18}$ diolefin and/or alkenylbenzene. Copolymers of ethylene and a $C_3$–$C_{20}$ α-olefin are especially preferred. Suitable unsaturated comonomers useful for polymerizing with ethylene include, for example, ethylenically unsaturated monomers, conjugated or nonconjugated dienes, polyenes, alkenylbenzenes, etc. Examples of such comonomers include $C_3$–$C_{20}$ α-olefins such as propylene, isobutylene, 1-butene, 1-hexene, 1-pentene, 4-methyl-1-pentene, 1-heptene, 1-octene, 1-nonene, 1-decene, and the like. Preferred comonomers include propylene, 1-butene, 1-pentene, 1-hexene, 4-methyl-1-pentene, 1-heptene, and 1-octene, and 1-octene is especially preferred. Other suitable monomers include styrene, halo- or alkyl-substituted styrenes, vinylbenzocyclobutane, 1,4-hexadiene, 1,7-octadiene, and naphthenics (e.g., cyclopentene, cyclohexene and cyclooctene).

The ethylene interpolymer has a differential scanning calorimetry (DSC) crystallinity of less than 26, preferably less than or equal to 15, weight percent (wt %). The preferred homogeneously branched ethylene polymers (such as, but not limited to, substantially linear ethylene polymers) have a single melting peak between −30 and 150° C., as determined using DSC, as opposed to traditional Ziegler-catalyst polymerized heterogeneously branched ethylene polymers (e.g., LLDPE and ULDPE or VLDPE) which have two or more melting points. The single melting peak is determined using a differential scanning calorimeter standardized with indium and deionized water. The DSC method uses about 5–7 mg sample sizes, a "first heat" to about 180° C. which is held for 4 minutes, a cool down at 10 C./min to −30 C. which is held for 3 minutes, and heat up at 10° C./min. to 150° C. to provide a "second heat" heat flow vs. temperature curve. Total heat of fusion of the polymer is calculated from the area under the curve.

The homogeneously branched ethylene polymer prior to irradiation, cure or crosslinking has a density at 23 C. of less than 0.90, preferably less than or equal to 0.89 and more preferably less than or equal to about 0.88, g/cm³. The homogeneously branched ethylene polymer prior to irradiation, cure or crosslinking has a density at 23 C. of greater than about 0.855, preferably greater than or equal to 0.860 and more preferably greater than or equal to about 0.865, g/cm³, as measured in accordance with ASTM D792. At densities higher than 0.89 g/cm³, the shrink-resistance at an elevated temperature (especially, low percent stress or load relaxation) is less than desirable. Ethylene interpolymers with a density of less than about 0.855 g/cm³ are not preferred because they exhibit low tenacity, very low melting point and handling problems, e.g., blocking and tackiness (at least prior to crosslinking).

Preferably, the ethylene interpolymer has a melt index of less than 50, more preferably of less than 10, gram/10 minute (g/10 min), as determined in accordance with ASTM D-1238, Condition 190 C/2.16 kilogram (kg).

The homogeneously branched, ethylene polymers used in the practice of this invention have less than 15, preferably less than 10, more preferably less than 5, and most preferably about zero (0), weight percent of the polymer with a degree of short chain branching less than or equal to 10methyls/1000 total carbons. In other words, the ethylene polymer does not contain any measurable high density polymer fraction (e.g., it does not contain a fraction having a density of equal to or greater than 0.94 g/cm³), as determined, for example, by using a temperature rising elution fractionation (TREF) (also known as analytical temperature rising elution fractionation (ATREF)) technique, or infrared or $^{13}C$ nuclear magnetic resonance (NMR) analysis. The composition (monomer) distribution (CD) of an ethylene interpolymer (also frequently called the short chain branching distribution (SCBD)) can be readily determined from TREF as described, for example, by Wild et al., *Journal of Polymer Science, Poly. Phys. Ed.*, Vol. 20, p. 441 (1982), or in U.S. Pat. Nos. 4,798,081 or 5,008,204; or by L. D. Cady, "The Role of Comonomer Type and Distribution in LLDPE Product Performance," SPE Regional Technical Conference, Quaker Square Hilton, Akron, Ohio, October 1–2, pp. 107–119 (1985). The composition distribution of the ethylene interpolymer can also be determined using $^{13}C$ NMR analysis in accordance with techniques described in U.S. Pat. Nos. 5,292,845, 5,089,321 and 4,798,081, and by J. C. Randall, *Rev. Macromol. Chem. Phys.*, C29, pp. 201–317. The composition distribution and other compositional information can also be determined using crystallization analysis fractionation such as the CRYSTAF fractionalysis package available commercially from PolymerChar, Valencia, Spain.

The substantially linear ethylene polymers used in the present invention are a unique class of compounds that are further described in U.S. Pat. Nos. 5,272,236, 5,278,272 and 5,665,800.

Substantially linear ethylene polymers differ significantly from the class of polymers conventionally known as homogeneously branched linear ethylene polymers described above and, for example, U.S. Pat. No. 3,645,992. As an important distinction, substantially linear ethylene polymers do not have a linear polymer backbone in the conventional sense of the term "linear" as is the case for homogeneously branched linear ethylene polymers.

"Linear" means that the ethylene polymer does not have long chain branching. In other words, the polymer chains comprising the bulk linear ethylene polymer have an absence of long chain branching, as in the case of traditional linear low density polyethylene polymers or linear high density polyethylene polymers made using Ziegler polymerization processes (e.g., U.S. Pat. No. 4,076,698), sometimes called heterogeneous polymers. The term "linear" does not refer to bulk high pressure branched polyethylene, ethylene/vinyl acetate copolymers, or ethylene/vinyl alcohol copolymers which are known to those skilled in the art to have numerous long chain branches.

The term "homogeneously branched linear ethylene polymer" refers to polymers having a narrow short chain branching distribution and an absence of long chain branching. Such "linear" uniformly branched or homogeneous polymers include those made as described in U.S. Pat. No. 3,645,992, and those made using so-called single-site catalysts in a batch reactor having relatively high ethylene concentrations (as described in U.S. Pat. Nos. 5,026,798 and 5,055,438), and those made using constrained geometry catalysts in a batch reactor also having relatively high olefin concentrations (as described in U.S. Pat. No. 5,064,802 and EP 0 416 815 A2). Suitable homogeneously branched linear ethylene polymers for use in the invention are sold under the designation of TAFMER by Mitsui Chemical Corporation and under the designations of EXACT and EXCEED by Exxon Chemical Company.

The term "substantially linear ethylene polymer" as used herein means that the bulk ethylene polymer is substituted, on average, with about 0.01 long chain branches/1000 total carbons to about 3 long chain branches/1000 total carbons (wherein "total carbons" includes both backbone and branch carbons). Preferred polymers are substituted with about 0.01 long chain branches/1000 total carbons to about 1 long chain branches/1000 total carbons, more preferably from about 0.05 long chain branches/1000 total carbons to about 1 long chain branched/1000 total carbons, and especially from about 0.3 long chain branches/1000 total carbons to about 1 long chain branches/1000 total carbons.

"Backbone" refers to a discrete molecule, and "polymer" or "bulk polymer" refers, in the conventional sense, to the polymer as formed in a reactor. For the polymer to be a "substantially linear ethylene polymer", the polymer must have at least enough molecules with long chain branching such that the average long chain branching in the bulk polymer is at least from about 0.01 long chain branches/1000 total carbons to about 3 long chain branches/1000 total carbons.

The term "bulk polymer" as used herein means the polymer which results from the polymerization process as a mixture of polymer molecules and, for substantially linear ethylene polymers, includes molecules having an absence of long chain branching as well as molecules having long chain branching. Thus a "bulk polymer" includes all molecules formed during polymerization. For the substantially linear polymers, not all of the molecules of the bulk polymer have long chain branching, but a sufficient amount do such that the average long chain branching content of the bulk polymer positively affects the melt rheology (i.e., the shear viscosity and melt fracture properties) as described herein below and elsewhere in the literature.

"Long chain branching (LCB)" and similar terms mean a chain length of at least about 6 carbons above which the length cannot be distinguished using $^{13}C$ nuclear magnetic resonance spectroscopy. The long chain branch can be as long as about the same length as the length of the polymer backbone. "Short chain branching (SCB)" and similar terms mean a chain length of the same number of carbons as in the residue of the comonomer after it has been incorporated into the polymer molecule backbone. For example, substantially linear ethylene/1-octene polymers has backbones with long chain branches of at least seven (7) carbons in length, but it also has short chain branches of only six (6) carbons in length.

Long chain branching can be distinguished from short chain branching by using $^{13}C$ nuclear magnetic resonance (NMR) spectroscopy and to a limited extent, e.g. for ethylene homopolymers, it can be quantified using the method of Randall, (*Rev. Macromol.Chem. Phys.*, C29 (2&3), p. 285–297). However as a practical matter, current $^{13}C$ nuclear magnetic resonance spectroscopy cannot determine the length of a long chain branch in excess of about six (6) carbon atoms and as such, this analytical technique cannot distinguish between a seven (7) carbon branch and a seventy (70) carbon branch. The long chain branch can be as long as about the same length as the length of the polymer backbone.

Although conventional $^{13}C$ nuclear magnetic resonance spectroscopy cannot determine the length of a long chain branch in excess of six carbon atoms, there are other known techniques useful for quantifying or determining the presence of long chain branches in ethylene polymers, including ethylene/1-octene interpolymers. For example, U.S. Pat. No. 4,500,648 teaches that long chain branching frequency (LCB) can be represented by the equation $LCB=b/M_w$, wherein b is the weight average number of long chain branches per molecule and $M_w$ is the weight average molecular weight. The molecular weight averages and the long chain branching characteristics are determined by gel permeation chromatography and intrinsic viscosity methods, respectively.

Two other useful methods for quantifying or determining the presence of long chain branches in ethylene polymers, including ethylene/1-octene interpolymers, are gel permeation chromatography coupled with a low angle laser light scattering detector (GPC-LALLS) and gel permeation chromatography coupled with a differential viscometer detector (GPC-DV). The use of these techniques for long chain branch detection and the underlying theories have been well documented in the literature. See, e.g., Zimm, G. H. and Stockmayer, W. H., *J. Chem. Phys.*, 17, 1301 (1949) and Rudin, A., *Modern Methods of Polymer Characterization*, John Wiley & Sons, New York (1991) pp. 103–112.

Substantially linear ethylene polymers also differ significantly from the class of polymers known conventionally as heterogeneously branched traditional Ziegler-catalyst polymerized linear ethylene interpolymers (for example, ultra low density polyethylene (ULDPE), linear low density polyethylene (LLDPE) or high density polyethylene (HDPE) made, for example, using the technique disclosed in U.S. Pat. No. 4,076,698, in that substantially linear ethylene interpolymers are homogeneously branched polymers. Further, substantially linear ethylene polymers also differ from the class of heterogeneously branched ethylene polymers in that substantially linear ethylene polymers are characterized as essentially lacking a measurable high density or crystalline polymer fraction as determined using a TREF technique.

For substantially linear ethylene polymers, the empirical effect of the presence of long chain branching is manifested as enhanced rheological properties which are quantified and expressed in terms of gas extrusion rheometry (GER) results and/or melt flow, $I_{10}/I_2$, increases.

The preferred homogeneously branched, substantially linear ethylene polymer for use in the present invention is characterized as having (a) melt flow ratio, $I_{10}/I_2 \geq 5.63$;

(b) a molecular weight distribution, $M_w/M_n$, as determined by gel permeation chromatography and defined by the equation:

$$(M_w/M_n) \leq (I_{10}/I_2) - 4.63;$$

(c) a gas extrusion rheology such that the critical shear rate at onset of surface melt fracture for the substantially linear ethylene polymer is at least 50 percent greater than the critical shear rate at the onset of surface melt fracture for a linear ethylene polymer, in which the substantially linear ethylene polymer and the linear ethylene polymer comprise the same comonomer or comonomers, the linear ethylene polymer has an $I_2$ and $M_w/M_n$ within ten percent of the substantially linear ethylene polymer, and in which the respective critical shear rates of the substantially linear ethylene polymer and the linear ethylene polymer are measured at the same melt temperature using a gas extrusion rheometer;

(d) a single DSC melting peak between −30 and 150 C.; and (e) a density less than or equal to about 0.890 g/cm³.

Determination of the critical shear rate and critical shear stress in regards to melt fracture as well as other rheology properties such as "rheological processing index" (PI), is performed using a gas extrusion rheometer (GER). The gas extrusion rheometer is described by M. Shida, R. N. Shroff and L. V. Cancio in *Polymer Engineering Science, Vol. 17*, No. 11, p. 770 (1977) and in *Rheometers for Molten Plastics* by John Dealy, published by Van Nostrand Reinhold Co. (1982) on pp. 97–99.

The processing index (PI) is measured at a temperature of 190 C., at nitrogen pressure of 2500 psig using a 0.0296 inch (752 micrometers) diameter (preferably a 0.0143 inch diameter die for high flow polymers, e.g. 50–100 $I_2$ melt index or greater), 20:1 L/D die having an entrance angle of 180°. The GER processing index is calculated in millipoise units from the following equation:

$$PI = 2.15 \times 10^6 \text{ dyne/cm}^2 / (1000 \times \text{shear rate}),$$

where: $2.15 \times 10^6$ dyne/cm² is the shear stress at 2500 psi, and the shear rate is the shear rate at the wall as represented by the following equation:

$$32 Q'/(60 \text{ sec/min})(0.745)(\text{Diameter} \times 2.54 \text{ cm/in})^3, \text{ where:}$$

Q' is the extrusion rate (g/min), 0.745 is the melt density of polyethylene (g/cm³), and Diameter is the orifice diameter of the capillary (inches). The PI is the apparent viscosity of a material measured at apparent shear stress of $2.15 \times 10^6$ dyne/cm². For substantially linear ethylene polymers, the PI is less than or equal to 70 percent of that of a conventional linear ethylene polymer having an $I_2$, $M_w/M_n$ and density each within ten percent of the substantially linear ethylene polymer.

An apparent shear stress vs. apparent shear rate plot is used to identify the melt fracture phenomena over a range of nitrogen pressures from 5250 to 500 psig using the die or GER test apparatus previously described. According to Ramamurthy in *Journal of Rheology*, 30(2), 337–357, 1986, above a certain critical flow rate, the observed extrudate irregularities may be broadly classified into two main types: surface melt fracture and gross melt fracture.

Surface melt fracture occurs under apparently steady flow conditions and ranges in detail from loss of specular gloss to the more severe form of "sharkskin". In this disclosure, the onset of surface melt fracture is characterized at the beginning of losing extrudate gloss at which the surface roughness of extrudate can only be detected by 40× magnification. The critical shear rate at onset of surface melt fracture for the substantially linear ethylene polymers is at least 50 percent greater than the critical shear rate at the onset of surface melt fracture of a linear ethylene polymer having about the same $I_2$ and $M_w/M_n$. Preferably, the critical shear stress at onset of surface melt fracture for the substantially linear ethylene polymers of the invention is greater than about $2.8 \times 10^6$ dyne/cm².

Gross melt fracture occurs at unsteady flow conditions and ranges in detail from regular (alternating rough and smooth, helical, etc.) to random distortions. For commercial acceptability, (e.g., in blown film products), surface defects should be minimal, if not absent. The critical shear rate at onset of surface melt fracture (OSMF) and critical shear stress at onset of gross melt fracture (OGMF) will be used herein based on the changes of surface roughness and configurations of the extrudates extruded by a GER. For the substantially linear ethylene polymers used in the invention, the critical shear stress at onset of gross melt fracture is preferably greater than about $4 \times 10^6$ dyne/cm².

For the processing index determination and for the GER melt fracture determination, substantially linear ethylene polymers are tested without inorganic fillers and do not have more than 20 ppm aluminum catalyst residue. Preferably, however, for the processing index and melt fracture tests, substantially linear ethylene polymers do contain antioxidants such as phenols, hindered phenols, phosphites or phosphonites, preferably a combination of a phenol or hindered phenol and a phosphite or a phosphonite.

The molecular weight distributions of polyolefin, particularly ethylene, polymers are determined by gel permeation chromatography (GPC) on a Waters 150 C. high temperature chromatographic unit equipped with a differential refractometer and three columns of mixed porosity. The columns are supplied by Polymer Laboratories and are commonly packed with pore sizes of $10^3$, $10^4$, $10^5$ and $10^6$ Å. The solvent is 1,2,4-trichlorobenzene, from which about 0.3 percent by weight solutions of the samples are prepared for injection. The flow rate is about 1.0 milliliters/minute, unit operating temperature is about 140° C. and the injection size is about 100 microliters.

The molecular weight determination with respect to the polymer backbone is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in *Journal of Polymer Science*, Polymer Letters, Vol. 6, p. 621, 1968:

$$M_{polyethylene} = a * (M_{polystyrene})b.$$

In this equation, a=0.4316 and b=1.0. Weight average molecular weight, $M_w$, is calculated in the usual manner according to the following formula: $Mj=(\Sigma w_i(M_i^j))^j$. Where $w_i$ is the weight fraction of the molecules with molecular weight $M_i$ eluting from the GPC column in fraction i and j=1 when calculating $M_w$, and j=-1 when calculating $M_n$.

In those embodiments of the invention in which at least one homogeneously branched ethylene polymer is used, the $M_w/M_n$ is preferably less than 3.5, more preferably less than 3.0, most preferably less than 2.5, and especially in the range of from about 1.5 to about 2.5 and most especially in the range from about 1.8 to about 2.3.

Substantially linear ethylene polymers are known to have excellent processability despite having a relatively narrow molecular weight distribution (that is, the $M_w/M_n$ ratio is typically less than about 3.5). Surprisingly, unlike homogeneously and heterogeneously branched linear ethylene polymers, the melt flow ratio ($I_{10}/I_2$) of substantially linear ethylene polymers can be varied essentially independently of the molecular weight distribution, $M_w/M_n$. Accordingly, especially when good extrusion processability is desired, the preferred ethylene polymer for use in the present invention is a homogeneously branched substantially linear ethylene interpolymer.

The polyolefin can be blended with other polymers. Suitable polymers for blending with the polyolefin are commercially available from a variety of suppliers and include, but are not limited to, other polyolefins such as an ethylene polymer (e.g., low density polyethylene (LDPE), ULDPE, medium density polyethylene (MDPE), LLDPE, HDPE, homogeneously branched linear ethylene polymer, substantially linear ethylene polymer, graft-modified ethylene polymer ESI, ethylene vinyl acetate interpolymer, ethylene acrylic acid interpolymer, ethylene ethyl acetate interpolymer, ethylene methacrylic acid interpolymer, ethylene methacrylic acid ionomer, and the like), polycarbonate, polystyrene, polypropylene (e.g., homopolymer polypropylene, polypropylene copolymer, random block polypropylene interpolymer and the like), thermoplastic polyurethane, polyamide, polylactic acid interpolymer, thermoplastic block polymer (e.g. styrene butadiene copolymer, styrene butadiene styrene triblock copolymer, styrene ethylenebutylene styrene triblock copolymer and the like), polyether block copolymer (e.g., PEBAX), copolyester polymer, polyester/polyether block polymers (e.g., HYTEL), ethylene carbon monoxide interpolymer (e.g., ethylene/carbon monoxide (ECO), copolymer, ethylene/acrylic acid/carbon monoxide (EAACO) terpolymer, ethylene/methacrylic acid/carbon monoxide (EMAACO) terpolymer, ethylene/vinyl acetate/carbon monoxide (EVACO) terpolymer and styrene/carbon monoxide (SCO)), polyethylene terephthalate (PET), chlorinated polyethylene, and the like and mixtures thereof. In other words, the polyolefin used in the practice of this invention can be a blend of two or more polyolefins, or a blend of one or more polyolefins with one or more polymers other than a polyolefin. If the polyolefin used in the practice of this invention is a blend of one or more polyolefins with one or more polymers other than a polyolefin, then the polyolefins comprise at least about 1, preferably at least about 50 and more preferably at least about 90, wt % of the total weight of the blend.

In one embodiment, the ethylene interpolymer is blended with a polypropylene polymer. Suitable polypropylene polymers for use in the invention, including random block propylene ethylene polymers, are available from a number of manufacturers, such as, for example, Montell Polyolefins and Exxon Chemical Company. Suitable polypropylene polymers from Exxon are supplied under the designations ESCORENE and ACHIEVE.

Suitable graft-modified polymers for use in this invention are well known in the art, and include the various ethylene polymers bearing a maleic anhydride and/or another carbonyl-containing, ethylenically unsaturated organic radical. Representative graft-modified polymers are described in U.S. Pat. No. 5,883,188, such as a homogeneously branched ethylene polymer graft-modified with maleic anhydride.

Suitable polylactic acid (PLA) polymers for use in the invention are well known in the literature (e.g., see D. M. Bigg et al., "Effect of Copolymer Ratio on the Crystallinity and Properties Is of Polylactic Acid Copolymers", ANTEC '96, pp. 2028–2039; WO 90/01521; EP 0 515203A and EP 0 748 846 A2. Suitable polylactic acid polymers are supplied commercially by Cargill Dow under the designation Eco-PLA.

Suitable thermoplastic polyurethane polymers for use in the invention are commercially available from The Dow Chemical Company under the designation PELLATHANE.

Suitable polyolefin carbon monoxide interpolymers can be manufactured using well known high pressure free-radical polymerization methods. However, they may also be manufactured using traditional Ziegler-Natta catalysis, or with the use of so-called homogeneous catalyst systems such as those described and referenced above.

Suitable free-radical initiated high pressure carbonyl-containing ethylene polymers such as ethylene acrylic acid interpolymers can be manufactured by any technique known in the art including the methods taught by Thomson and Waples in U.S. Pat. Nos. 3,520,861, 4,988,781; 4,599,392 and 5,384,373.

Suitable ethylene vinyl acetate interpolymers for use in the invention are commercially available from various suppliers, including Exxon Chemical Company and Du Pont Chemical Company.

Suitable ethylene/alkyl acrylate interpolymers are commercially available from various suppliers. Suitable ethylene/acrylic acid interpolymers are commercially available from The Dow Chemical Company under the designation PRIMACOR. Suitable ethylene/methacrylic acid interpolymers are commercially available from Du Pont Chemical Company under the designation NUCREL.

Chlorinated polyethylene (CPE), especially chlorinated substantially linear ethylene polymers, can be prepared by chlorinating polyethylene in accordance with well known techniques. Preferably, chlorinated polyethylene comprises equal to or greater than 30 weight percent chlorine. Suitable chlorinated polyethylenes for use in the invention are commercially supplied by The Dow Chemical Company under the designation TYRIN.

Photoinitiator

The photoinitiators used in the practice of the invention are aromatic ketones, e.g., benzophenones or monoacetals of 1,2-diketones. The primary photoreaction of the monacetals is the homolytic cleavage of the $\alpha$-bond to give acyl and dialkoxyalkyl radicals. This type of $a\alpha$-cleavage is known as a Norrish Type I reaction which is more fully described in W. Horspool and D. Armesto, Organic Photochemistry: *A Comprehensive Treatment*, Ellis Horwood Limited, Chichester, England, 1992; J. Kopecky, *Organic Photochemistry: A Visual Approach*, VCH Publishers, Inc., New York, N.Y. 1992; N. J. Turro, et al., *Acc. Chem. Res.*, 1972, 5, 92; and J. T. Banks, et al., *J. Am. Chem. Soc.*, 1993, 115, 2473. The synthesis of monoacetals of aromatic 1,2 diketones, Ar—CO—C(OR)$_2$—Ar' is described in U.S. Pat. No. 4,190,602 and Ger. Offen. 2,337,813. The preferred compound from this class is 2,2-dimethoxy-2-phenylacetophenone, $C_6H_5$—CO—C(OCH$_3$)$_2$—$C_6H_5$, which is commercially available from Ciba-Geigy as Irgacure 651. Examples of other aromatic ketones useful in the practice of this invention as photoinitiators are Irgacure 184, 369, 819, 907 and 2959, all available from Ciba-Geigy.

Photocrosslinkers

In one embodiment of the invention, the photoinitiator is used in combination with a photocrosslinker. Any photocrosslinker that will upon the generation of free radicals, link two or more polyolefin backbones together through the formation of covalent bonds with the backbones can be used in this invention. Preferably these photocrosslinkers are polyfunctional, i.e., they comprise two or more sites that upon activation will form a covalent bond with a site on the backbone of the polyolefin polymer. Representative photocrosslinkers include, but are not limited to polyfunctional vinyl or allyl compounds such as, for example, triallyl cyanurate, triallyl isocyanurate, pentaerthritol tetramethacrylate, ethylene glycol dimethacrylate, diallyl maleate, dipropargyl maleate, dipropargyl monoallyl cyanurate and the like. Preferred photocrosslinkers for use in the present invention are compounds which have polyfunctional (i.e. at least two) moieties. Particularily preferred photocrosslinkers are triallycyanurate (TAC) and triallylisocyanurate (TAIC).

Photoinitiator/Photocrosslinker

Certain compounds act as both a photoinitiator and a photocrosslinker in the practice of this invention. These compounds are characterized by the ability to generate two or more reactive species (e.g., free radicals, carbenes, nitrenes, etc.) upon exposure to UV-light and to subsequently covalently bond with two polymer chains. Any compound that can preform these two functions can be used in the practice of this invention, and representative compounds include the sulfonyl azides described in U.S. Pat. Nos. 6,211,302 and 6,284,842.

Secondary Crosslinking

In another embodiment of this invention, the polyolefin polymer is subjected to secondary crosslinking, i.e., crosslinking other than and in addition to photocrosslinking. In this embodiment, the photoinitiator is used either in combination with a nonphotocrosslinker, e.g., a silane, or the polyolefin polymer is subjected to a secondary crosslinking procedure, e.g, exposure to E-beam radiation. Representative examples of silane crosslinkers are described in U.S. Pat. No. 5,824,718, and crosslinking through exposure to E-beam radiation is described in U.S. Pat. Nos. 5,525,257 and 5,324,576. The use of a photocrosslinker in this embodiment is optional.

Mixing the Photoadditives with the Polyolefin Polymer

At least one photoadditive, i.e., photoinitiator and optional photocrosslinker, can be introduced to the polyolefin polymer by any method known in the art. However, preferably the photoadditive(s) is (are) introduced via a masterbatch concentrate comprising the same or different base resin as the polyolefin polymer. Preferably, the photoadditive concentration for the masterbatch is relatively high e.g., about 25 weight percent (based on the total weight of the concentrate).

The at least one photoadditive is introduced to the polyolefin polymer in any effective amount. Preferably, the at least one photoadditive introduction amount is from about 0.001 to about 5, more preferably from about 0.005 to about 2.5 and most preferably from about 0.015 to about 1, wt % (based on the total weight of the polyolefin polymer).

The photoinitiator(s) and optional photocrosslinker(s) can be added during different stages of the fiber or film manufacturing process. If photoadditives can withstand the extrusion temperature, a polyolefin resin can be mixed with additives before being fed into the extruder, e.g., via a masterbatch addition. Alternatively, additives can be introduced into the extruder just prior the slot die, but in this case the efficient mixing of components before extrusion is important. In another approach, polyolefin fibers can be drawn without photoadditives, and a photoinitiator and/or photocrosslinker can be applied to the extruded fiber via a kiss-roll, spray, dipping into a solution with additives, or by using other industrial methods for post-treatment. The resulting fiber with photoadditive(s) is then cured via electromagnetic radiation in a continuous or batch process. The photo additives can be blended with the polyolefin using conventional compounding equipment, including single and twin-screw extruders.

Cure

The power of the electromagnetic radiation and the irradiation time are chosen so as to allow efficient crosslinking without polymer degradation and/or dimensional defects. The preferred process is described in EP 0 490 854 B1. Photoadditive(s) with sufficient thermal stability is (are) premixed with a polyolefin resin, extruded into a fiber, and irradiated in a continuous process using one energy source or several units linked in a series. There are several advantages to using a continuous process compared with a batch process to cure a fiber or sheet of a knitted fabric which are collected onto a spool.

Irradiation may be accomplished by the use of UV-radiation. Preferably, UV-radiation is employed up to the intensity of 100 J/cm$^2$. The irradiation source can be any UV-light generator operating in a range of about 50 watts to about 25000 watts with a power output capable of supplying the desired dosage. The wattage can be adjusted to appropriate levels which may be, for example, 1000 watts or 4800 watts or 6000 watts or higher or lower. Many other apparati for UV-irradiating polymeric materials are known in the art. The irradiation is usually carried out at a dosage between about 3 J/cm$^2$ to about 500 J/scm$^2$, preferably between about 5 J/cm² to about 100 J/cm². Further, the irradiation can be carried out conveniently at room temperature, although higher and lower temperatures, for example 0° C. to about 60° C., may also be employed. The photocrosslinking process is faster at higher temperatures. Preferably, the irradiation is carried out after shaping or fabrication of the article. In a preferred embodiment, the polyolefin polymer which has been incorporated with a photoadditive is irradiated with UV-radiation at about 10 J/cm² to about 50 J/cm².

Other Additives

Antioxidants, e.g., Irgafos 168, Irganox 1010, Irganox 3790, and chimassorb 944 made by Ciba Geigy Corp., may be added to the ethylene polymer to protect against undo degradation during shaping or fabrication operation and/or to better control the extent of grafting or crosslinking (i.e., inhibit excessive gelation). In-process additives, e.g. calcium stearate, water, fluoropolymers, etc., may also be used for purposes such as for the deactivation of residual catalyst and/or improved processability. Tinuvin 770 (from Ciba-Geigy) can be used as a light stabilizer.

The polyolefin polymer can be filled or unfilled. If filled, then the amount of filler present should not exceed an amount that would adversely affect either heat-resistance or elasticity at an elevated temperature. If present, typically the amount of filler is between 0.01 and 80 wt % based on the total weight of the polyolefin polymer (or if a blend of a polyolefin polymer and one or more other polymers, then the total weight of the blend). Representative fillers include kaolin clay, magnesium hydroxide, zinc oxide, silica and calcium carbonate. In a preferred embodiment, in which a filler is present, the filler is coated with a material that will prevent or retard any tendency that the filler might otherwise have to interfere with the crosslinking reactions. Stearic acid is illustrative of such a filler coating.

Fiber and other Article Manufacture

Various homofil fibers can be made from the polyolefin polymer of the present invention, including staple fibers, spunbond fibers or melt blown fibers (using, e.g., systems as disclosed in U.S. Pat. Nos. 4,340,563, 4,663,220, 4,668,566 or 4,322,027, and gel spun fibers (e.g., the system disclosed in U.S. Pat. No. 4,413,110). Staple fibers can be melt spun into the final fiber diameter directly without additional drawing, or they can be melt spun into a higher diameter and subsequently hot or cold drawn to the desired diameter using conventional fiber drawing techniques.

Bicomponent fibers can also be made from the polyolefin polymers of this invention. Such bicomponent fibers have the polyolefin polymer of the present invention in at least one portion of the fiber. For example, in a sheath/core bicomponent fiber (i.e., one in which the sheath concentrically surrounds the core), the polyolefin can be in either the sheath or the core. Typically and preferably, the polyolefin polymer is the sheath component of the bicomponent fiber but if it is the core component, then the sheath component must be such that it does not prevent the crosslinking of the core, i.e., the sheath component is transparent or translucent to UV-radiation such that sufficient UV-radiation can pass through it to substantially crosslink the core polymer. Different polyolefin polymers can also be used independently as the sheath and the core in the same fiber, preferably where both components are elastic and especially where the sheath component has a lower melting point than the core component. Other types of bicomponent fibers are within the scope of the invention as well, and include such structures as side-by-side conjugated fibers (e.g., fibers having separate regions of polymers, wherein the polyolefin of the present invention comprises at least a portion of the fiber's surface).

The shape of the fiber is not limited. For example, typical fiber has a circular cross-sectional shape, but sometimes fibers have different shapes, such as a trilobal shape, or a flat (i.e., "ribbon" like) shape. The elastic fiber disclosed herein is not limited by the shape of the fiber.

Fiber diameter can be measured and reported in a variety of fashions. Generally, fiber diameter is measured in denier per filament. Denier is a textile term which is defined as the grams of the fiber per 9000 meters of that fiber's length. Monofilament generally refers to an extruded strand having a denier per filament greater than 15, usually greater than 30. Fine denier fiber generally refers to fiber having a denier of about 15 or less. Microdenier (aka microfiber) generally refers to fiber having a diameter not greater than about 100 micrometers. For the elastic fibers of this invention, the diameter can be widely varied, with little impact upon the elasticity of the fiber. The fiber denier, however, can be adjusted to suit the capabilities of the finished article and as such, would preferably be: from about 0.5 to about 30 denier/filament for melt blown; from about 1 to about 30 denier/filament for spunbond; and from about 1 to about 20,000 denier/filament for continuous wound filament. Nonetheless, preferably, the denier is greater than 40, more preferably greater than or equal to 55 and most preferably greater than or equal to 65. These preferences are due to the fact that typically durable apparel employ fibers with deniers greater than about 40.

The elastic polyolefin polymer can also be shaped or fabricated into elastic films, coatings, sheets, strips, tapes, ribbons and the like. The elastic film, coating and sheet of the present invention may be fabricated by any method known in the art, including blown bubble processes (e.g., simple bubble as well as biaxial orientation techniques such trapped bubble, double bubble and tenter framing), cast extrusion, injection molding processes, thermoforming processes, extrusion coating processes, profile extrusion, and sheet extrusion processes. Simple blown bubble film processes are described, for example, in *The Encyclopedia of Chemical Technology*, Kirk-Othmer, Third Edition, John Wiley & Sons, New York, 1981, Vol. 16, pp. 416–417 and Vol. 18, pp. 191–192. The cast extrusion method is described, for example, in Modern Plastics Mid-October 1989 Encyclopedia Issue, Volume 66, Number 11, pages 256 to 257. Injection molding, thermoforming, extrusion coating, profile extrusion, and sheet extrusion processes are described, for example, in Plastics Materials and Processes, Seymour S. Schwartz and Sidney H. Goodman, Van Nostrand Reinhold Company, New York, 1982, pp. 527–563, pp. 632–647, and pp. 596–602.

The elastic strips, tapes and ribbons of the present invention can be prepared by any known method, including the direct extrusion processing or by post-extrusion slitting, cutting or stamping techniques. Profile extrusion is an example of a primary extrusion process that is particularly suited to the preparation of tapes, bands, ribbons and the like.

The elastic fiber can be used with other fibers such as PET, nylon, cotton, Kevlar™, etc. to make elastic fabrics. As an added advantage, the heat (and moisture) resistance of certain elastic fibers can enable polyester PET fibers to be dyed at ordinary PET dyeing conditions. The other commonly used elastic fibers, especially spandex (e.g., Lycra™), can only be used at less severe PET dyeing conditions to prevent degradation of properties.

Fabrics made from the elastic fibers of this invention include woven, nonwoven and knit fabrics. Nonwoven fabrics can be made various by methods, e.g., spunlaced (or hydrodynamically entangled) fabrics as disclosed in U.S. Pat. Nos. 3,485,706 and 4,939,016, carding and thermally bonding staple fibers; spunbonding continuous fibers in one continuous operation; or by melt blowing fibers into fabric and subsequently calendering or thermally bonding the resultant web. These various nonwoven fabric manufacturing techniques are well known to those skilled in the art and the disclosure is not limited to any particular method. Other structures made from such fibers are also included within the scope of the invention, including e.g., blends of these novel fibers with other fibers (e.g., poly(ethylene terephthalate) or cotton).

Fabricated articles which can be made using the elastic fibers and fabrics of this invention include elastic composite articles (e.g., diapers) that have elastic portions. For example, elastic portions are typically constructed into diaper waist band portions to prevent the diaper from falling and leg band portions to prevent leakage (as shown in U.S. Pat. No. 4,381,781 (Sciaraffa), the disclosure of which is incorporated herein by reference). Often, the elastic portions promote better form fitting and/or fastening systems for a good combination of comfort and reliability. The inventive elastic fibers and fabrics can also produce structures which combine elasticity with breathability. For example, the inventive elastic fibers, fabrics and/or films may be incorporated into the structures disclosed in U.S. provisional patent application 60/083,784, filed May 1, 1998.

The inventive elastic fibers, films and fabrics can also be used in various structures as described in U.S. Pat. No. 2,957,512. For example, layer 50 of the structure described in U.S. Pat. No. '512 (i.e., the elastic component) can be replaced with the inventive elastic fibers and fabrics, especially where flat, pleated, creped, crimped, etc., nonelastic materials are made into elastic structures. Attachment of the inventive elastic fibers and/or fabric to nonelastic fibers, fabrics or other structures can be done by melt bonding or with adhesives. Gathered or shirted elastic structures can be produced from the inventive elastic fibers and/or fabrics and nonelastic components by pleating the non-elastic component (as described in U.S. Pat. No. '512) prior to attachment, pre-stretching the elastic component prior to attachment, or heat shrinking the elastic component after attachment.

The inventive elastic fibers also can be used in a spunlaced (or hydrodynamically entangled) process to make novel structures. For example, U.S. Pat. No. 4,801,482 discloses an elastic sheet (12) which can now be made with the novel elastic fibers/films/fabric described herein.

Continuous elastic filaments as described herein can also be used in woven applications where high resilience is desired.

U.S. Pat. No. 5,037,416 describes the advantages of a form fitting top sheet by using elastic ribbons (see member 19 of U.S. Pat. No. '416). The inventive elastic fibers could serve the function of member 19 of U.S. Pat. No. '416, or could be used in fabric form to provide the desired elasticity.

In U.S. Pat. No. 4,981,747 (Morman), the inventive elastic fibers and/or fabrics disclosed herein can be substituted for elastic sheet 122, which forms a composite elastic material including a reversibly necked material.

The inventive elastic fibers can also be a melt blown elastic component, as described in reference 6 of the drawings of U.S. Pat. No. 4,879,170 (Radwanski. U.S. Pat. No. '170 generally describes elastic co-form material and manufacturing processes.

Elastic panels can also be made from the inventive elastic fibers and fabrics disclosed herein, and can be used, for example, as members 18, 20, 14, and/or 26 of U.S. Pat. No. 4,940,464. The inventive elastic fibers and fabrics described herein can also be used as elastic components of composite side panels (e.g., layer 86 of U.S. Pat. No. '464).

The elastic materials of the present invention can also be rendered pervious or "breathable" by any method well known in the art including by apperturing, slitting, microperforating, mixing with fibers or foams, or the like and combinations thereof. Examples of such methods include, U.S. Pat. No. 3,156,242 by Crowe, Jr., U.S. Pat. No. 3,881,489 by Hartwell, U.S. Pat. No. 3,989,867 by Sisson and U.S. Pat. No. 5,085,654 by Buell.

The following examples are provided to further illustrate and illuminate the present invention but are not intended to limit the invention to the specific embodiments set forth. Unless indicated to the contrary, all parts and percentages are by weight.

Specific Embodiments

Test Methods

Polymer Descriptions.

Polymer A is a thermoplastic elastic polyethylene resin (a homogeneously branched, substantially linear ethylene/1-octene copolymer having a density of 0.87 g/cm$^3$ and a melt index of 5 g/10 min) which is prepared with 500 ppm (parts per million) Irganox 1076 and 800 ppm Irgafos PEPQ (an organic phosphonite), both antioxidants purchased from Ciba-Geigy. Polymer B is a CMP, specifically a polyvinylcyclohexane copolymer having a molecular weight of 63,000 and density of 0.91 g/cm$^3$ prepared by a full hydrogenation of a styrene/butadiene copolymer having 32 weight percent styrene and 40 percent of 1,2-vinyl groups and with 1000 ppm Irganox 1010 and 300 ppm XP 136 lactone, both antioxidants purchased from Ciba-Geigy. Polymer C is a thermoplastic polyolefin resin available from The Dow Chemical Company as ESI DE 400.01 (a substantially random ethylene/styrene interpolymer with 30 weight percent styrene and a melt index 10 g/10 min). It contains an antiblock package of 1000 ppm poly(dimethyl siloxane) binder and 2000 ppm talc.

Insoluble Polymer Fraction.

The gel percentage of a polymer was determined by ASTM D-2765 method. The mass of the film sample to be tested is recorded (M1), the sample placed in a soxhlet extractor above a flask with xylene, and the solvent refluxed for 24 hours. The residual polymer in the soxhlet extractor is then dried and the mass again recorded (M2). The percent insoluble fraction is detemined by the following formula: M2/M1*100.

Dynamic Mechanical Analysis (DMA).

Dynamic mechanical testing was performed using a Rheometric's RSA-2 instrument with Rhios 4.4.4 software for machine control and data collection. The frequency was 6.28 rad/s, strain was 0.05% or 0.10%, and the temperature range was −100° C. to 200° C. (with the ramp of 2° C./min). Testing was conducted on films (with the thickness of 0.15 mm or 0.50 mm) or fibers.

Hot Stage Optical Microscopy.

The Olympus Vanox optical microscope with Linkan Scientific hot plate (model THM 600) was used. The temperature increase was controlled by the Linkan PR600 controller. Four fibers are placed on the glass microscope slide in such orientation, that they cross each other. The slide with fibers is placed on the hot plate and the temperature is increased from 20° C. to 240° C., at the rate of 10° C./min. Photographs were taken at each 5° C. intervals and the images were stored in a computer.

EXAMPLES

Example One

Crosslinking of Polymer A Film with Irgacure 651

An amount (98.6 weight percent) of Polymer A, 1.0 weight percent Irgacure photoinitiator available from Ciba- Geigy, and 0.4 weight percent of Irganox 1010 hindered phenolic antioxidant were blended using Haake blender. The materials were loaded into the blending unit at 180° C. and 50 revolutions per minute, and then blended at the same temperature at 100 revolutions per minute for 5 minutes. The resulting blend was compression molded into a film having a thickness of approximately 0.50 mm. Samples of the films were UV-cured for the time indicated in Table One using an American Ultraviolet Company unit (a lamp with a broad range of wavelengths; lamp intensity=200 WPI, the total lamp power=1 kW).

The percent insoluble polymer fraction was determined for each of the samples, and is reported in Table One. As set forth in Table One, the crosslinked samples of the invention demonstrated measurable crosslinking.

Dynamic mechanical analysis (DMA) of the film of Example 1(b) was performed, with the results being graphically depicted in FIG. 1. As illustrated in FIG. 1, the storage modulus E' (related to the storage of energy as a potential energy and its release in the periodic deformation) showed flat line up to 250° C. which is indicative of crosslinking. The loss modulus E" (associated with the dissipation of energy as a heat when the material is deformed) showed a measurable value up to 250° C., indicating that the film did not melt.

Example Two

Crosslinking of Polymer A Fiber with Irgacure 651

An amount (97.7 weight percent) of Polymer A, 2.0 weight percent of Irgacure 651 photoinitiator, 0.2 weight percent Irganox 1010 hindered phenolic antioxidant, and 0.1 weight percent Tinuvin 770 hindered amine light stabilizer available from Ciba-Geigy were blended in the amounts indicated in Table One using Haake blender and the blending procedure described in Example One. The resultant blend was spun into a 40 to 165 denier monofilament fiber. A one-inch extruder with four heating zones (with temperatures of 165° C., 180° C., 200° C., and 205° C.) and a round die with orifice diameter of 0.750 mm was used. The extruded filament was solidified using cold air at 10° C. A spin-draw ratio (velocity of draw roll/velocity at spinneret orifice) between 25 and 50 was used, and the drawn fiber was wound on a Comoli monofilament surface driven low tension winder. Samples of the fibers were UV-cured using the equipment described in Example One, with the cure times being indicated in Table One.

The percent insoluble polymer fraction was determined for each of the samples, and is reported in Table One. As set forth in Table One, the crosslinked samples of the invention demonstrated measurable crosslinking.

Example Three

Crosslinking of Polymer A Film with Irgacure 651 and TAIC

An amount (97.6 weight percent) of Polymer A, 1.0 weight percent Irgacure 651 photoinitiator, 1.0 weight percent of triallylisocyanurate (TAIC) photocrosslinker, and 0.4 weight percent Irganox 1010 hindered phenolic antioxidant were blended using Haake blender, and the blending procedure described in Example One. The resulting blends were compression molded into films having a thickness of approximately 0.15 mm. Samples of the resultant films were UV-cured for the time indicated in Table One using the equipment described in Example One.

The percent insoluble polymer fraction was determined for each of the samples, and is reported in Table One. As set forth in Table One, the crosslinked samples of the invention demonstrated measurable crosslinking. Further, a comparison of the samples of Examples 1(b), 1(c) and 3(a) demonstrates that the addition of TAIC or the substitution of TAIC for a portion of the Irgacure 651 permit more rapid attainment of a crosslinked system.

Example Four

Crosslinking of Polymer A Film and Fiber with Anthrone and TAC

An amount (97.5 weight percent) of Polymer A, 1.0 weight percent anthrone photoinitiator, 1.0 weight percent triallylcyanurate (TAC) photocrosslinker, and 0.5 weight percent Irganox 1010 hindered phenolic antioxidant were blended using Haake blender, and the blending procedure described in Example One. The resulting blends were formed in approximately 0.15 mm thick compression molded films and 80 to 100 denier monofilaments using the same procedure and described in Example Two. The resultant films and fibers were UV-cured for the time indicated in Table One, using the same equipment and procedure as described in Example One.

The percent insoluble polymer fraction was determined for each of the samples, and is reported in Table One. As set forth in Table One, the crosslinked samples of the invention demonstrated measurable crosslinking.

Figure 2B:
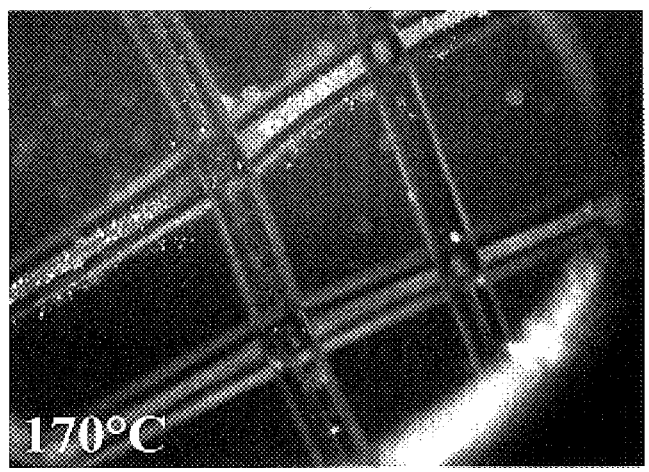
Figure 2C:
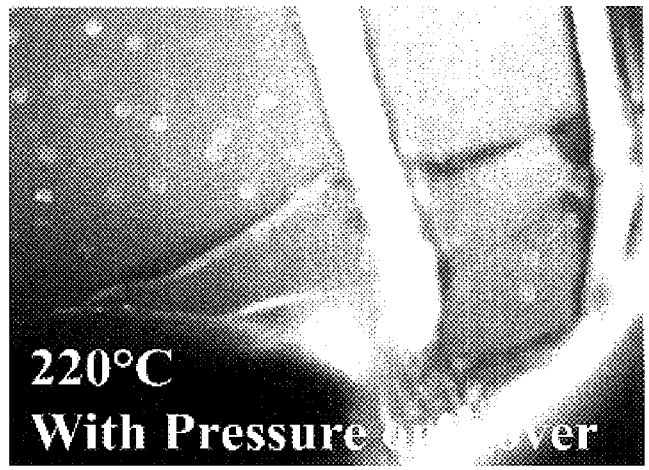

The fiber of Example 4(f) was also evaluated using hot stage optical microscopy, with the results being set forth in FIGS. 2A–C. As illustrated in these Figures, the fibers did not fuse up to 170° C., and retained their shape up to 220° C.

Example Five

Crosslinking of Polymer A Film with Benzophenone

An amount (98.7 weight percent) of Polymer A, 1.0% benzophenone, 0.10% Irganox 3790 antioxidant, 0.10% Chimassorb 944, and 0.10% Tinuvin 770 were blended using Haake blender and the blending procedure described in Example One. The resulting blend was compression molded into a film having a thickness of approximately 0.15 mm.

Samples of this film were UV cured for the time indicated in Table One using the equipment described in Example One. The percent insoluble polymer fraction was determined for each of the samples, and is reported in Table One. As set forth in Table One, the crosslinked samples of the invention demonstrated measurable crosslinking.

Figure 3:
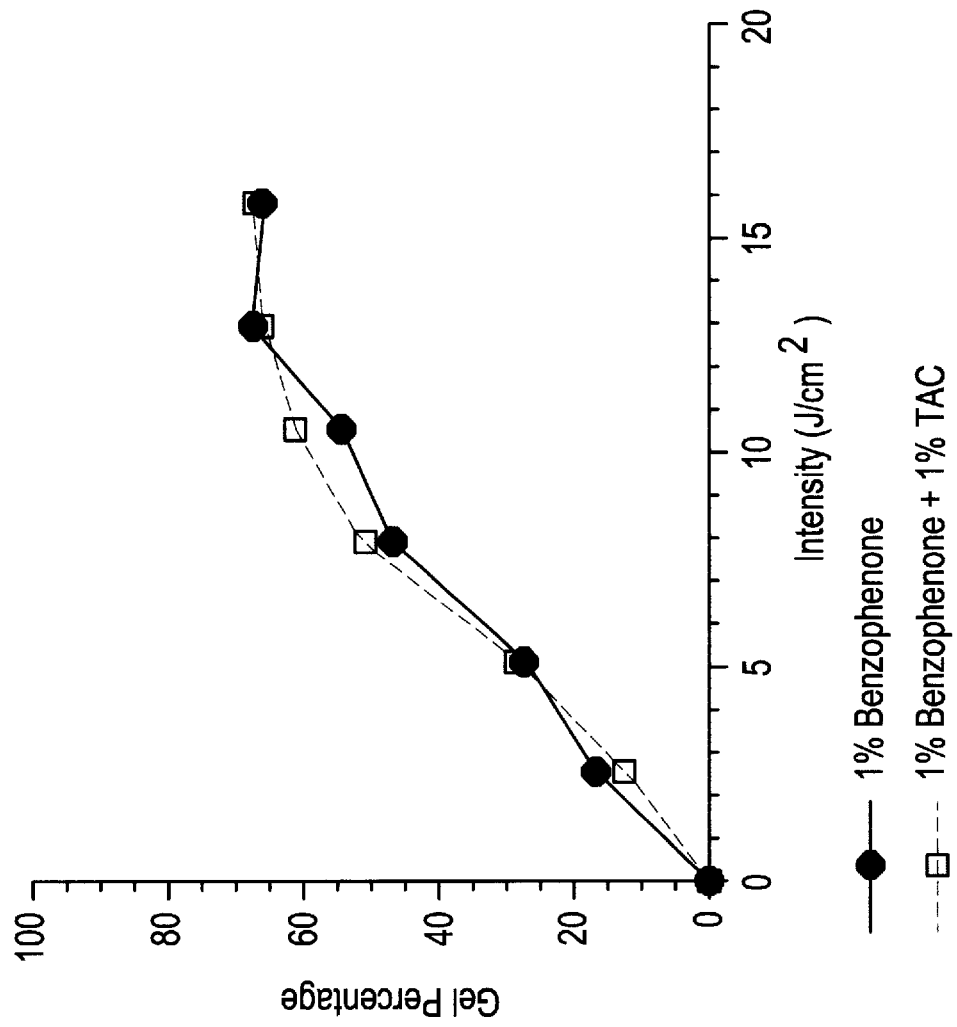
FIG. 3 is a graph showing the percent insoluble polymer fraction of the films prepared in Examples 5 and 6.

In another experiment, the compression-molded film described above was UV cured at different intensities and the percent insoluble polymer fraction was determined for each of the samples, as illustrated in FIG. 3. Measurable crosslinking of these samples is in agreement with the crosslinking of samples 5(b) and 5(c).

Example Six

Crosslinking of Polymer A Film with Benzophenone and TAC

Polymer A, 1.00% benzophenone, 0.25% triallylcyanurate (TAC), 0.10% Irganox 3790, 0.10% Chimassorb 944, and 0.10% Tinuvin 770 were blended using Haake blender and the blending procedure described in Example One. The resulting blend was compression molded into a film having a thickness of approximately 0.15 mm. This film was UV cured at different intensities and the percent insoluble polymer fraction was determined for each of the samples, as illustrated in FIG. 3.

Example Seven

Crosslinking of Polymer B Film and a Fiber with Irgacure 651

Two blends were prepared with Polymer B, 0.5 weight percent Irganox 1010 hindered phenolic antioxidant, and Irgacure 651 photoinitiator in the amounts indicated in Table One. The same procedure for Haake blending was used as in Example One. One blend, prepared with 2.0 weight percent Irgacure 651, was compression molded into a film having a thickness of approximately 0.15 mm. Another blend, prepared with 1.5 weight percent Irgacure 651, was spun into a 70 to 180 denier monofilament fiber using the same one-inch extruder and a similar spinning procedure as described in Example Two. The four heating zones had temperatures of 175° C., 200° C., 210° C., and 220° C., and an orifice diameter of a round die was 1.000 mm. Samples of the film and the fiber were UV-cured using the equipment described in Example One, with the cure times being indicated in Table One.

The percent insoluble polymer fraction was determined for each of the samples, and is reported in Table One. As set forth in Table One, the crosslinked samples of the invention demonstrated measurable crosslinking.

Figure 4A:
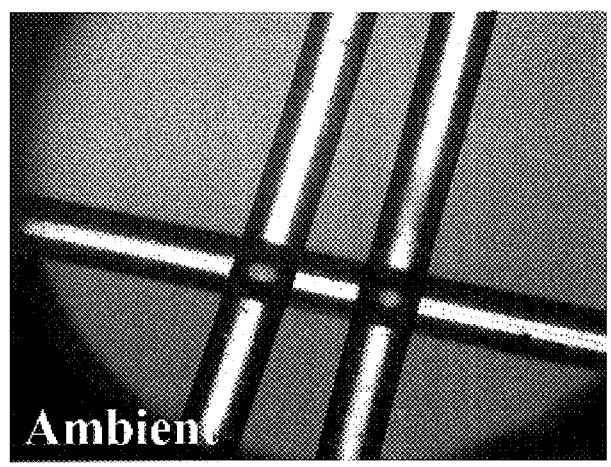
FIGS. 4A–4C are micrographs of the fiber produced in Example 7.
Figure 4B:
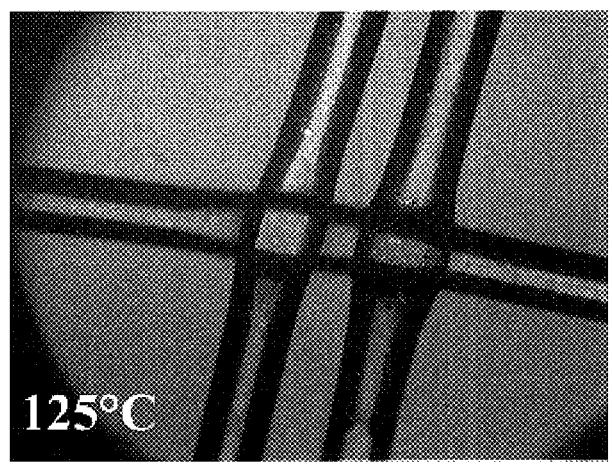
Figure 4C:
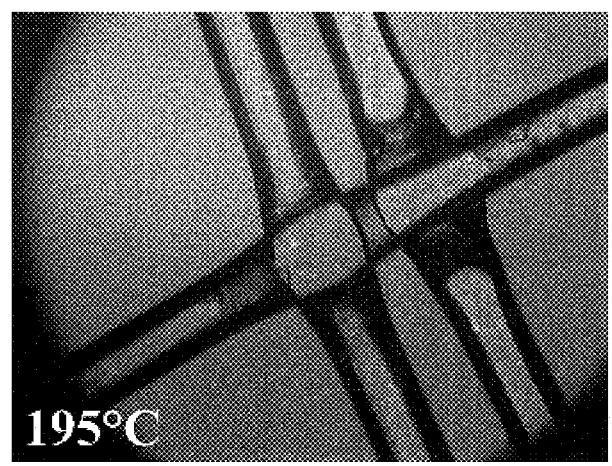

Hot stage optical microscopy of the fiber of Example 7(e) was performed. The resultant micrograph, taken at 195° C., is set forth in FIGS. 4A–C. As set forth in FIG. 4C, at 195° C. the fibers still did not melt, and they were still not completely fused, indicating good dimensional stability at elevated temperatures.

Example Eight

Crosslinking of Polymer B Film with Anthrone and TAC

An amount (97.5 weight percent) of Polymer B, 1.0 weight percent anthrone photoinitiator, 1.0 weight percent triallylcyanurate (TAC) photocrosslinker, and 0.5 weight percent Irganox 1010 hindered phenolic antioxidant were blended using Haake blender and the blending procedure described in Example One. The resulting blends were formed in approximately 0.15 mm thick compression molded film. Samples of this film were UV-cured for the time indicated in Table One, using the same equipment described in Example One.

The percent insoluble polymer fraction was determined for each of the samples, and is reported in Table One. As set forth in Table One, the crosslinked samples of the invention demonstrated measurable crosslinking.

Example Nine

Crosslinking of Polymer C Film with Irgacure 651

Two blends were prepared with Polymer C, 0.4 weight percent Irganox 1010 hindered phenolic antioxidant, and Irgacure 651 photoinitiator in the amounts indicated in Table One. Haake blender. and the blending procedure described in Example One were used The resulting blends were compression molded into films having a thickness of approximately 0.15 mm. Samples of the resultant films were UV-cured for the time indicated in Table One using the equipment described in Example One.

Figure 5:
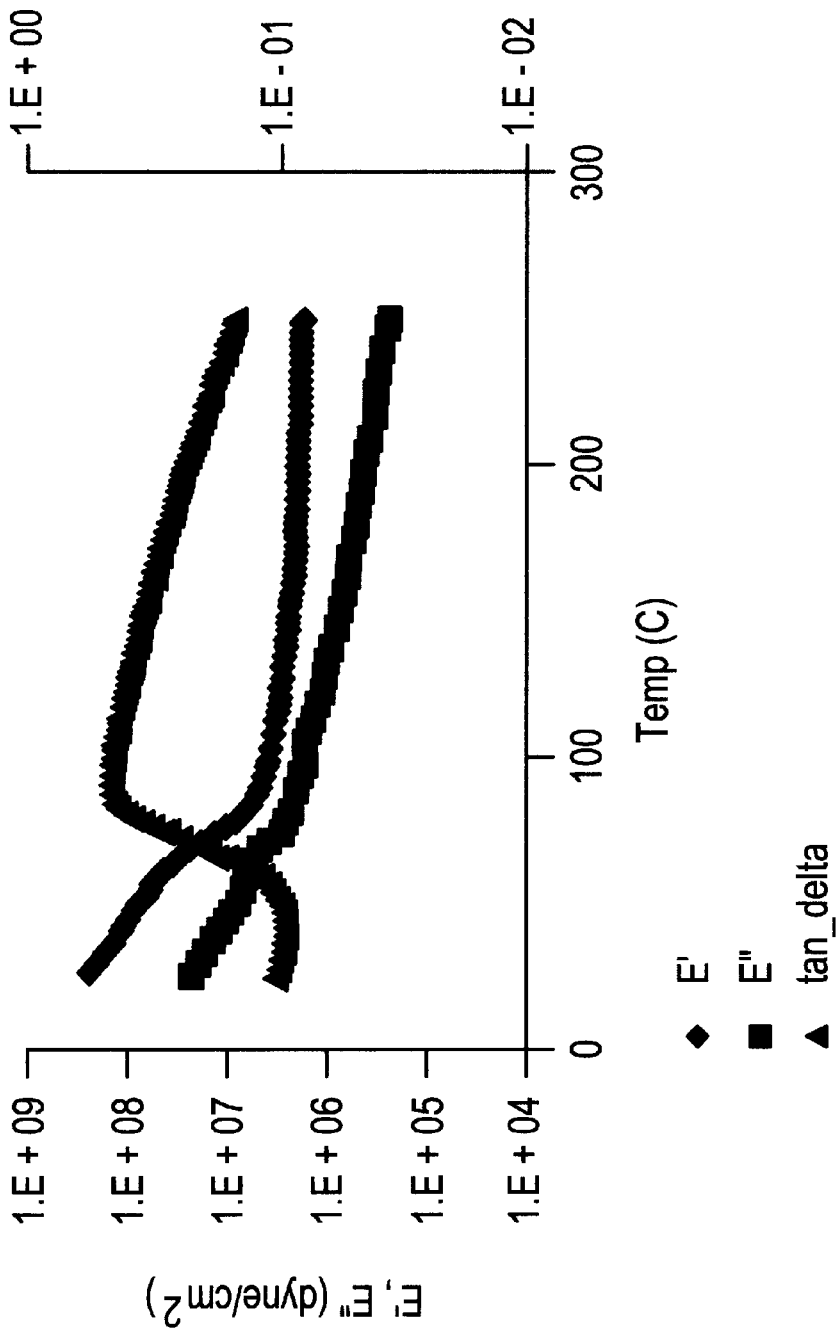
FIG. 5 is a graph showing the storage modules E' of the film prepared in Example 9.

Dynamic mechanical analysis (DMA) of the film of Example 9(a) was performed with the results being graphically depicted in FIG. 5. As set forth in FIG. 5, this film showed flat E' line up to 250° C. which is indicative of crosslinking. Furthermore, the measurable value of E" up to 250° C. indicates that the film did not melt. The DMA indicates that the film of Example 9(a) exhibits good dimensional stability at elevated temperatures.

The percent insoluble polymer fraction was determined for the remaining samples, and is reported in Table One. As set forth in Table One, the crosslinked samples of the invention demonstrated measurable crosslinking.

Example Ten

Crosslinking of Polymer C Film with Anthrone and TAC

An amount (97.5) weight percent) of Polymer C, 1.0 weight percent anthrone photoinitiator, 1.0 weight percent triallylcyanurate (TAC) photocrosslinker, and 0.5 weight percent Irganox 1010 hindered phenolic antioxidant were blended using Haake blender and the blending procedure described in Example One. The resulting blends were formed in approximately 0.15 mm thick compression molded film. Samples of this film were UV-cured for the time indicted in Table One, using the same equipment described in Example One.

The percent insoluble polymer fraction was determined for each of the samples, and is reported in Table One. As set forth in Table One, the crosslinked samples of the invention demonstrated measurable crosslinking.

TABLE ONE

Comparative Data of Polyolefin Polymers Crosslinked with Different Photoadditives Under Varying UV-Cure Conidtions

| Example | Polymer | Photoadditive (wt %) | Sample | UV cure (min) | Insoluble fraction (%) |
|---|---|---|---|---|---|
| 1(a) | Polymer A | Irg 651 (1%) | film | 0 | 0 |
| 1(b) | | Irg 651 (1%) | film | 6 | 18 |
| 1(c) | | Irg 651 (2%) | film | 20 | 51 |
| 1(d) | | Irg 651 (2%) | film | 60 | 91 |
| 2(a) | Polymer A | Irg 651 (2%) | fiber | 3 | 23 |
| 2(b) | | Irg 651 (2%) | fiber | 20 | 58 |
| 3(a) | Polymer A | Irg 651 (1%) + TAIC (1%) | film | 6 | 69 |
| 3(b) | | Irg 651 (1%) + TAIC (1%) | film | 20 | 81 |
| 3(c) | | Irg 651 (1%) + TAIC (1%) | film | 60 | 76 |
| 4(a) | Polymer A | AN (1%) + TAC (1%) | film | 0 | 0 |
| 4(b) | | AN (1%) + TAC (1%) | film | 6 | 5 |
| 4(c) | | AN (1%) + TAC (1%) | film | 20 | 27 |
| 4(d) | | AN (1%) + TAC (1%) | film | 60 | 70 |
| 4(e) | | AN (1%) + TAC (1%) | fiber | 6 | 58 |
| 4(f) | | AN (1%) + TAC (1%) | fiber | 20 | 83 |
| 5(a) | Polymer A | BP (1%) | film | 0 | 0 |
| 5(b) | | BP (1%) | film | 6 | 70 |

TABLE ONE-continued

Comparative Data of Polyolefin Polymers
Crosslinked with Different Photoadditives
Under Varying UV-Cure Conidtions

| Example | Polymer | Photoadditive (wt %) | Sample | UV cure (min) | Insoluble fraction (%) |
|---|---|---|---|---|---|
| 5(c) | | BP (1%) | film | 20 | 82 |
| 6(a) | Polymer A | BP (1%) + TAC (0.25%) | film | | |
| 7(a) | Polymer B (CMP) | Irg 651 (2%) | film | 6 | 11 |
| 7(b) | | Irg 651 (2%) | film | 20 | 29 |
| 7(c) | | Irg 651 (2%) | film | 60 | 91 |
| 7(d) | | Irg 651 (1.5%) | fiber | 3 | 7 |
| 7(e) | | Irg 651 (1.5%) | fiber | 20 | 30 |
| 8(a) | Polymer B (CMP) | AN (1%) + TAC (1%) | film | 0 | 0 |
| 8(b) | | AN (1%) + TAC (1%) | film | 6 | 2 |
| 8(c) | | AN (1%) + TAC (1%) | film | 20 | 25 |
| 8(d) | | AN (1%) + TAC (1%) | film | 60 | 85 |
| 9(a) | Polymer C (ESI) | Irg 651 (1%) | film | 6 | |
| 9(b) | | Irg 651 (2%) | film | 0 | 0 |
| 9(c) | | Irg 651 (2%) | film | 20 | 28 |
| 9(d) | | Irg 651 (2%) | film | 60 | 41 |
| 10(a) | Polymer C (ESI) | AN (1%) + TAC (1%) | film | 0 | 0 |
| 10(b) | | AN (1%) + TAC (1%) | film | 6 | 6 |
| 10(c) | | AN (1%) + TAC (1%) | film | 20 | 13 |
| 10(d) | | AN (1%) + TAC (1%) | film | 60 | 35 |

Irg 651 = Irgacure 651; AN = Anthrone; BP = benzophenone; TAIC = triallylisocyanurate; TAC = triallylcyanurate In the examples reported in Table One above, the samples are in the form of a fiber or a film. Although this invention relates to fibers, results obtained with films are used for the illustrative purpose of showing which photoadditives and UV cure times lead to considerable polyolefin crosslinking. For all three types of polymers listed in Table One and for all photoadditives evaluated, after the longest UV cure (up to 60 minutes) the insoluble fraction increased to at least 30 percent. In several examples the UV cure of only 6 minutes was sufficient to reach the level over 30 percent insoluble fraction, and in many examples the insoluble fraction was larger than 60 percent. Examples One and Three show that for the homogeneously branched, substantially linear ethylene polymer with Irgacure 651 and TAIC photocrosslinker the insoluble fraction can reach a level above 60 percent after shorter UV cure than in the same polymer with Irgacure 651, but without TAIC.

Example Eleven

Crosslinking of Polymer C Fiber with BSA

Polymer C was spun into a monofilament fiber, using the equipment described in Example Two, and drawn directly through a bath with 1.0 wt % solution of 4,4'-oxybis (benzenesulfonyl azide) (BSA) in 1,2-dichloroethane. The resulting fiber was dried and UV-cured for 60 minutes at 254 nm in a Rayonet Photoreactor with eight 75-W tubes. Dynamic mechanical analysis of this fiber was performed, with the results graphically depicted in FIG. 6. As set forth in FIG. 6, this fiber showed flat E' line up to 200° C. which is indicative of crosslinking. Furthermore, the measurable value of E" up to 200° C. indicates that the fiber did not melt.

Dynamic mechanical analysis of a reference ESI DE 400.01 fiber without BSA treatment indicated that the fiber melted at ~100° C.

Although the invention has been described in considerable detail through the preceding examples, this detail is for the purpose of illustration. Many variations can be made without departing from the scope of the invention as described in the appended claims. All of the U.S. patents cited above are incorporated herein by reference.

What is claimed is:

1. A temperature-stables elastic, polyolefin filament fiber substantially crosslinked solely as a result of an aromatic ketone photoinitiator activated by exposure to ultraviolet radiation.

2. The fiber of claim 1 in which the photoinitiator is a monoacetal of a 1,2-diketone.

3. The fiber of claim 1 in which the photoinitiator is of formula 1:

$$Ar—CO—C(OR)2-Ar' \qquad (I)$$

in which each Ar is independently an aromatic radical and R is an aliphatic radical.

4. The fiber of claim 1 in which the photoinitiator is 2,2-dimethoxy-2-phenylacctophenone.

5. The fiber of any of claims 1 and 2–4 which the polyolefin is an ethylene interpolymer.

6. The fiber of any of claims 1 and 2–4 in which the polyolefin is a homogeneously branched ethylene polymer.

7. The fiber of any of claims 1 and 2–4 in which the polyolefin is a homogeneously branched, substantially linear ethylene polymer.

8. The fiber of any of claims 1 and 2–4 in which the polyolefin is a homogeneously branched, substantially liner ethylene polymer characterized as having:
   (a) a inch flow ratio, $I10/I2 \geq 5.63$;
   (b) a molecular weight distribution, $Mw/Mn$, as determined by gel permeation chromatography and defined by the equation:

$$(Mw/Mn) \leq (I10/I2) - 4.63;$$

(c) a gas extrusion rheology such that the critical shear rate at onset of surface melt fracture for the substantially linear ethylene polymer is at least 50 percent greater than the critical shear rate at the onset of surface melt fracture for a linear ethylene polymer, wherein the substantially linear ethylene polymer and the linear ethylene polymer comprise the same comonomer or comonomers, the linear ethylene polymer has an I2 and Mw/Mn within ten percent of the substantially linear ethylene polymer and wherein the respective critical shear rates of the substantially linear ethylene polymer and the linear ethylene polymer are measured at the same melt temperature using a gas extrusion rheometer; and
   (d) a density at 23 C of less than bout 0.895 g/cm3 as measured in accordance with ASTM D-792.

9. A temperature-stable, elastic, homogeneously branched, substantially linear ethylene polymer filament fiber substantially crosslinked as a result of a photoinitiator activated by exposure to ultraviolet radiation.

10. The fiber of claim 9 in which the photoinitiator is a free-radical photoinitiator.

11. The fiber of claim 9 in which the photoinitiator is an aromatic ketone photoinitiator.

12. The fiber of claim 9 in which the photoinitiator is a monoacetal of a 1,2-diketone.

13. The fiber of claim 9 in which the photoinitiator is of formula I:

$$Ar\text{—}CO\text{—}C(OR)2\text{-}Ar' \qquad (I)$$

in which each Ar is independently an aromatic radical and R is an aliphatic radical.

14. The fiber of claim 9 in which the photoinitiator is 2,2-dimethoxy-2-phenylacetophenone.

15. The fiber of claim 9 in which the substantial crosslinking is a result of activation of both a photoinitiator and a photocrosslinker by exposure to ultraviolet radiation.

16. The fiber of claim 15 in which the photocrosslinker is at least one of a polyfunctional vinyl or allyl compound, an azo compound and an organic peroxide.

17. The fiber of claim 15 in which the photocrosslinker is a polyfunctional vinyl or allyl compound.

18. The fiber of claim 15 in which the photocrosslinker is triallylcyanurate or triallylisocyanurate.

19. A substantially crosslinked, temperature-stable, elastic, polyolefin polymer filament fiber made by a process comprising the steps of (i) forming a substantially homogeneous blend X consisting of (a) a polyolefin and (b) an aromatic ketone photoinitiator, (ii) forming a fiber from the blend, and (iii) exposing the fiber to sufficient ultraviolet radiation to substantially crosslink the polyolefin.

20. A substantially crosslinked, temperature-stable, elastic, homogezieously branched, substantially linear ethylene polymer filament fiber made by a process comprising the steps of (i) forming a substantially homogeneous blend comprising (a) an ethylene polymer and (b) a photoinitiator, (ii) forming a fiber from the blend, and (iii) exposing the fiber to sufficient ultraviolet radiation to substantially crosslink the ethylene polymer.

21. The fiber of claim 20 which the photoinitiator is an aromatic ketone photoinitiator.

22. The fiber of claim 20 in which the blend further comprises a photocrosslinker.

23. The fiber of claim 22 in which the photocrosslinker is at least one of a polyfunctional vinyl or allyl compound, an azo compound and an organic peroxide.

24. The fiber of claim 22 which the photocrosslinker is a polyfunctional vinyl or allyl compound.

25. The fiber of claim 22 in which the photocrosslinker is triallylcyanurate or triallylisocyanurate.

26. The fiber of claim 19 or 20 in which the photoinitiator is present in an amount of at least about 0.001 weight percent based on the weight of the polymer.

27. The fiber of claim 19 or 20 in which the photoinitiator is a monoacetal of a 1,2-diketone.

28. The fiber of claim 19 or 20 in which the photoinitiator is of formula I:

$$Ar\text{—}CO\text{—}C(OR)2\text{-}Ar' \qquad (I)$$

in which each Ar is independently an aromatic radical and R is an aliphatic radical.

29. The fiber of claim 19 or 20 in which the photoinitiator is 2,2-dimethoxy-2-phenylacetophenone.

30. A substantially crosslinked, temperature-stable, elastic, polyolefin polymer filament fiber made by a process comprising the steps of (i) forming a fiber from a polyolefin, (ii) applying an aromatic ketone photoinitiator to the fiber, and (iii) exposing the fiber to sufficient ultraviolet radiation to substantially crosslink the polyolefin.

31. A substantially crosslinked, temperature-stable, elastic, homogeneously branched, substantially linear ethylene interpolymer filament fiber made by a process comprising the steps of (i) forming a fiber from a homogeneously branched, substantially linear ethylene interpolymer, (ii) applying a photoinitiator to the fiber, and (iii) exposing the fiber to sufficient ultraviolet radiation to substantially crosslink the polyolefin.

32. The fiber of claim 31 in which photoinitiator is an aromatic ketone photoinitiator.

33. The fiber of claim 31 in which the blend further comprises a photocrosslinker.

34. The fiber of claim 33 in which the photocrosslinker is at least one of a polyfunctional vinyl or allyl compound, an azo compound and an organic peroxide.

35. The fiber of claim 33 in which the photocrosslinker is a polyfunctional vinyl or allyl compound.

36. The fiber of claim 33 in which the photocrosslinker is triallylcyanurate or triallylisocyanurate.

37. The fiber of claim 30 or 31 in which the photoinitiator is present in an amount of at least about 0.001 weight percent based on the weight of the polymer.

38. The fiber of claim 30 or 31 in which the photoinitiator is a monoacetal of a 1,2-diketone.

39. The fiber of claim 30 or 31 in which the photoinitiator is of formula I:

$$Ar\text{—}CO\text{—}C(OR)2\text{-}Ar' \qquad (I)$$

in which each Ar is independently an aromatic radical and R is an aliphatic radical.

40. The fiber of claim 30 or 31 in which the photoinitiator is 2,2-diinethoxy-2-phenylacetophenone.

41. The fiber of any of claims 1, 9, 19, 20, 30 and 31 as a homofil fiber.

42. The fiber of any of claims 1, 9, 19, 20, 30 and 31 as a bicomponent fiber comprising a core and sheath morphology.

43. The fiber of claim 42 in which the crosslinked polymer forma the sheath of the fiber.

44. An elastic article comprising the fiber of any of claims 1, 9, 19, 20, 30 and 31.

45. A woven or knitted fabric comprising the elastic fiber of any of claims 1, 9, 19, 20, 30 and 31.

46. The fabric of claim 45 comprising at least one fiber in addition to the elastic fiber.

47. A nonwoven fabric comprising the elastic fiber of any of claims 1, 9, 19, 20, 30 and 31.

48. The fabric of claim 47 comprising at least one fiber in addition to the elastic fiber.

49. A temperature-stable, elastic, filament fiber comprising a polyolefin substantially crosslinked solely as a result of an aromatic ketone photoinitiator activated by exposure to ultraviolet radiation.

50. A yarn comprising the fiber of any of claims 1, 9, 19, 20, 30, 31 and 49.

51. A covered yarn comprising the fiber of any of claims 1, 9, 19, 20, 30, 31 and 49.

52. A temperature-stable, elastic, filament fiber comprising a polyolefin substantially crosslinked solely as a result of a photoinitiator/photocrosslinker activated by exposure to ultraviolet radiation.

53. The fiber of claim 52 in which the photoinitiator/photocrosslinker is a sulfonyl azide.

54. A process for making a substantially crosslinked, temperature-stable, elastic, polyolefin polymer filament fiber, the process comprising the steps of (i) forming a fiber from a polyolefin polymer, (ii) applying an aromatic ketone photoinitiator to die fiber, anti (iii) exposing the fiber to sufficient ultraviolet radiation to substantially crosslink the polymer.

55. A process for making a substantially crosslinked, temperature-stable, elastic, homogeneously branched, substantially linear ethylene polymer filament fiber, the process comprising the steps of (i) forming a fiber from a homogeneously branched, substantially linear ethylene polymer, (ii) applying a photoinitiator to the fiber, and (iii) exposing the fiber to sufficient ultraviolet radiation to substantially crosslink the polymer.

56. The process of claim 54 or 55 in which the photoinitiator is present in an amount of at last about 0.001 weight percent based on the weight of the polymer.

57. The process of claim 54 or 55 in which the fiber is exposed to the UV irradiation with the intensity between 5 J/cm2 and 100 J/cm2.

* * * * *

UNITED STATES PATENT AND TRADEMARK OFFICE
CERTIFICATE OF CORRECTION

PATENT NO. : 6,709,742 B2
DATED : March 23, 2004
INVENTOR(S) : Mladen Ladika et al.

It is certified that error appears in the above-identified patent and that said Letters Patent is hereby corrected as shown below:

Column 24,
Line 11, replace "stables" with -- stable, --.
Line 24, replace "phenylacctophenone" with -- phenylacetophenone --.
Line 35, replace "inch" with -- melt --

Column 25,
Line 23, delete "X".

Column 26,
Line 29, replace "diinethoxy" with -- dimethoxy --.
Line 36, replace "forma" with -- forms --.
Line 65, replace "die" with -- the -- and "anti" with -- and --.

Column 28,
Line 2, replace "last" with -- least --.

Signed and Sealed this

Eighth Day of June, 2004

JON W. DUDAS
*Acting Director of the United States Patent and Trademark Office*